United States Patent [19]
Koros et al.

[11] Patent Number: 5,484,441
[45] Date of Patent: Jan. 16, 1996

[54] RONGEUR SURGICAL INSTRUMENT

[76] Inventors: Tibor Koros; Gabriel Koros, both of 610 Flinn Ave., Moorpark, Calif. 93021

[21] Appl. No.: 780,431

[22] Filed: Oct. 23, 1991

Related U.S. Application Data

[63] Continuation-in-part of Ser. No. 716,577, Jun. 17, 1991, abandoned.

[51] Int. Cl.[6] ................................................ A61B 17/00
[52] U.S. Cl. .................................................. 606/79; 606/83
[58] Field of Search ................... 606/83, 84, 79, 606/184, 167, 151, 53; 81/57.44, 300; 604/22

[56] References Cited

U.S. PATENT DOCUMENTS

| | | | |
|---|---|---|---|
| 1,040,523 | 10/1902 | Vilbiss | 606/83 |
| 3,507,284 | 4/1970 | Simmons | 606/83 |
| 3,842,839 | 10/1974 | Malis | 606/83 |
| 4,545,374 | 10/1985 | Jacobson | 606/83 |
| 4,733,663 | 3/1988 | Farley | 606/83 |
| 4,777,948 | 10/1988 | Wright | 606/83 |
| 4,990,148 | 2/1991 | Worrick | 606/83 |
| 4,994,024 | 2/1991 | Falk | 606/83 |
| 5,061,269 | 10/1991 | Muller | 606/83 |

*Primary Examiner*—Michael A. Brown
*Attorney, Agent, or Firm*—Richard Slehofer

[57] ABSTRACT

A rongeur surgical instrument is disclosed which has an actuating mechanism providing a variable degree of mechanical advantage for operation of the cutting element in the instrument. During the cutting stroke the rate of movement steadily decreases, while the degree of precision of movement and the amount of torque increase throughout the stroke. The instrument also has an improved shaft design which maintains cutting edge alignment with the footplate anvil surface, and also provides a mechanism for preventing cut portions of body material from aggregating near the distal end of the shaft and interfering with the cutting operation. In addition, the grip portion of the instrument has an adjustable spur member to allow the grip portion to comfortably fit a variety of hand sizes.

36 Claims, 11 Drawing Sheets

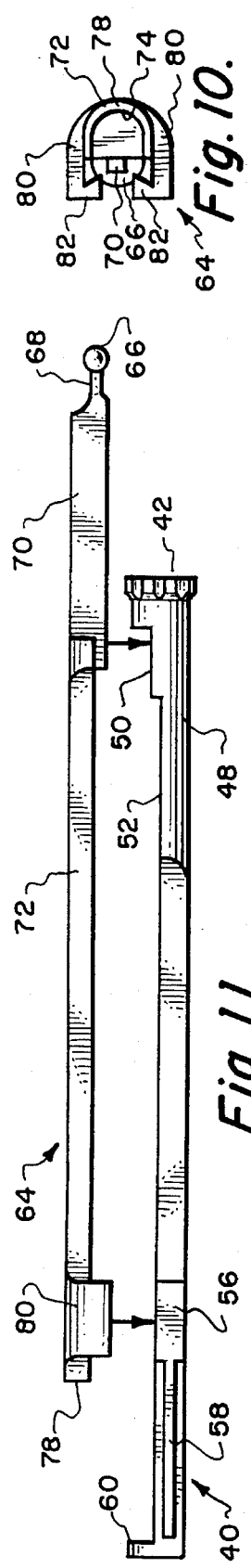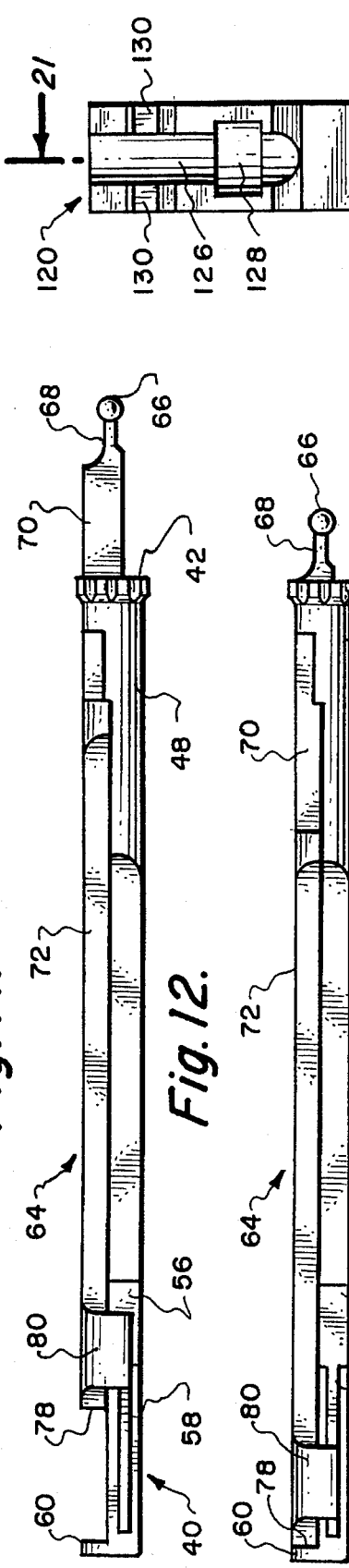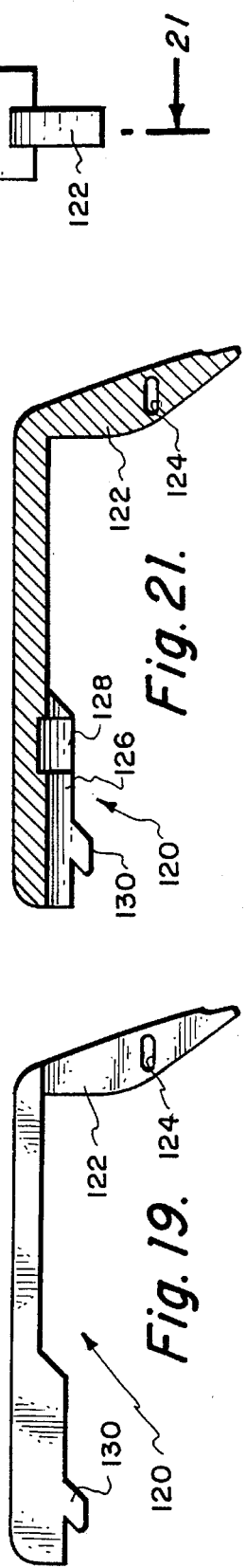

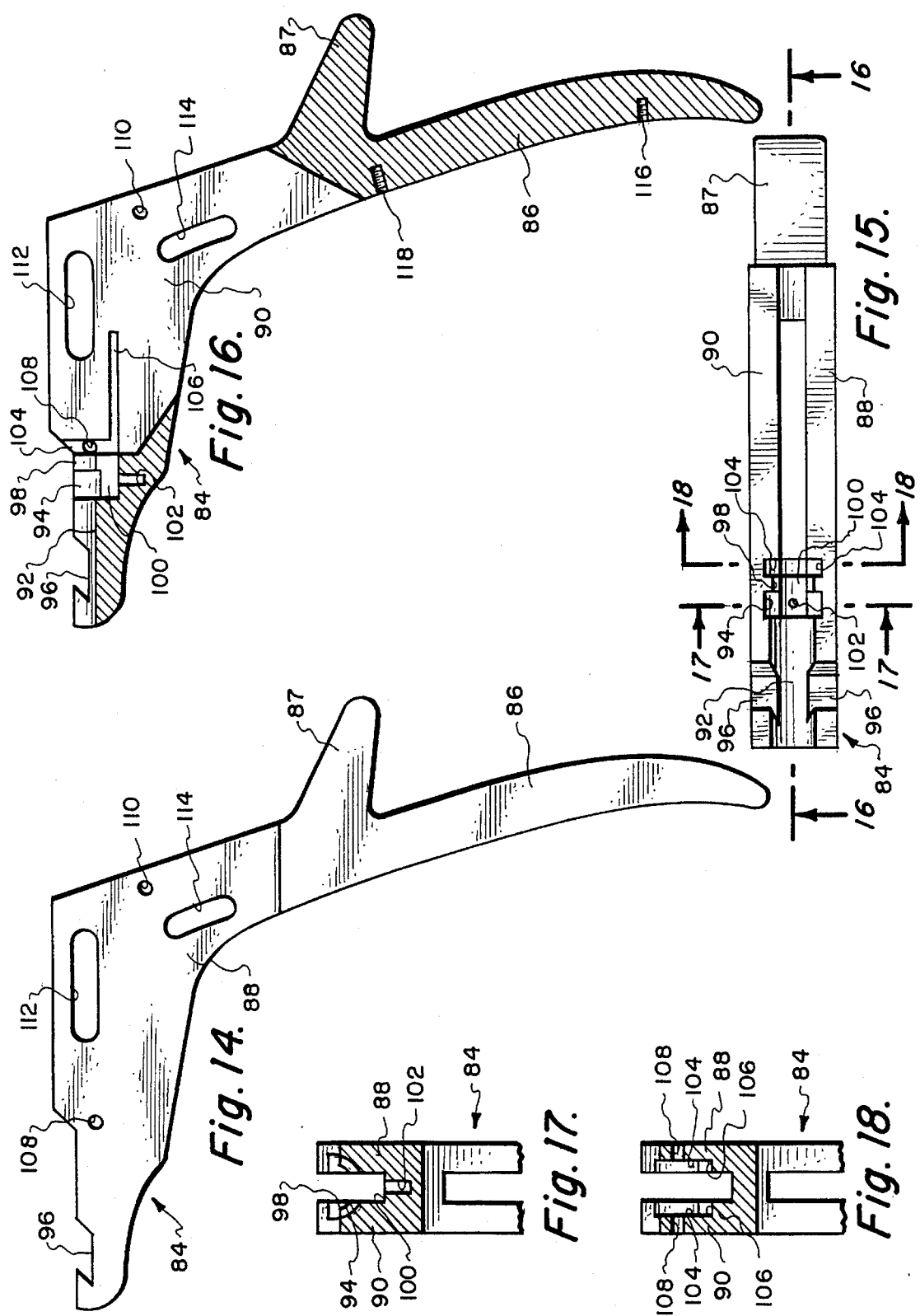

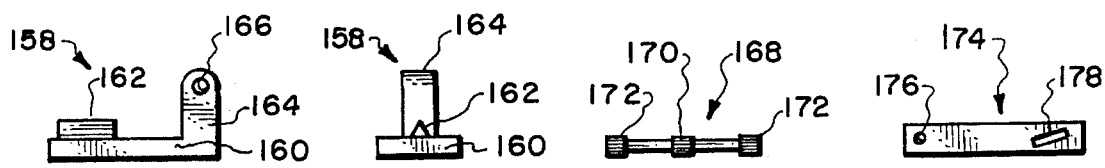
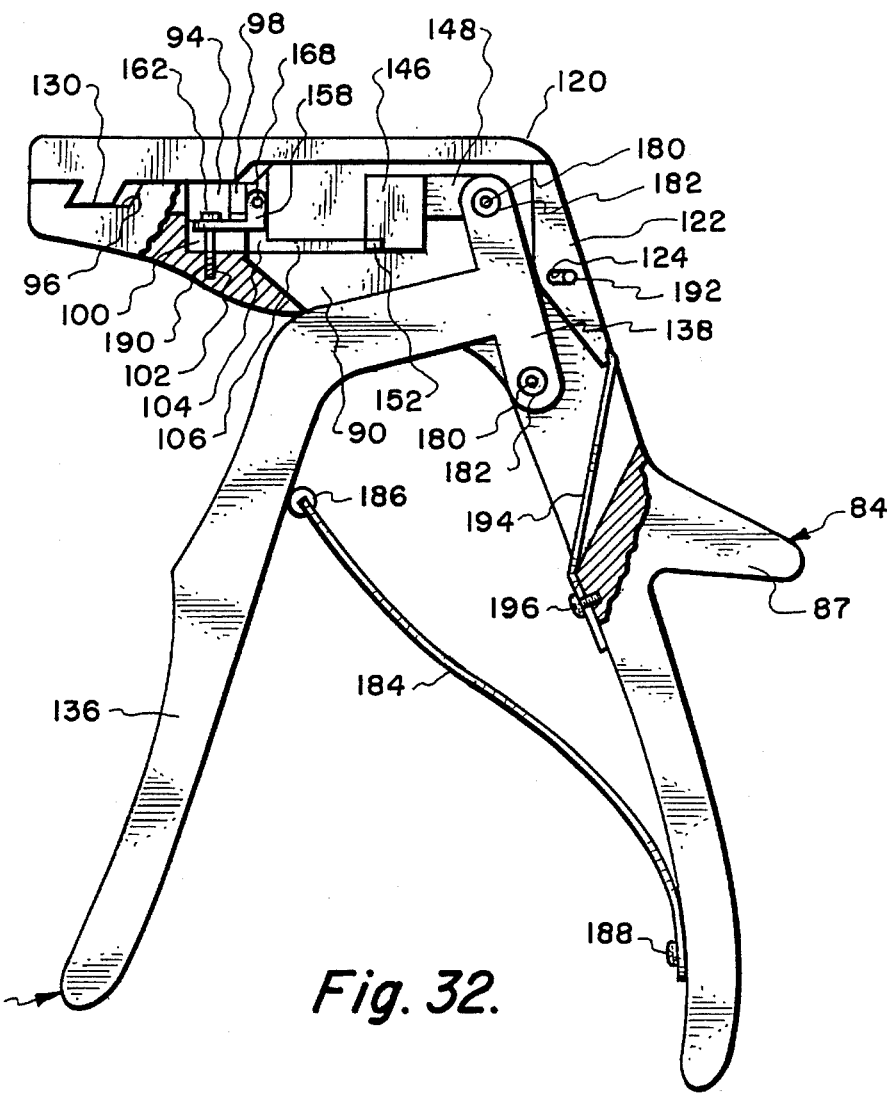

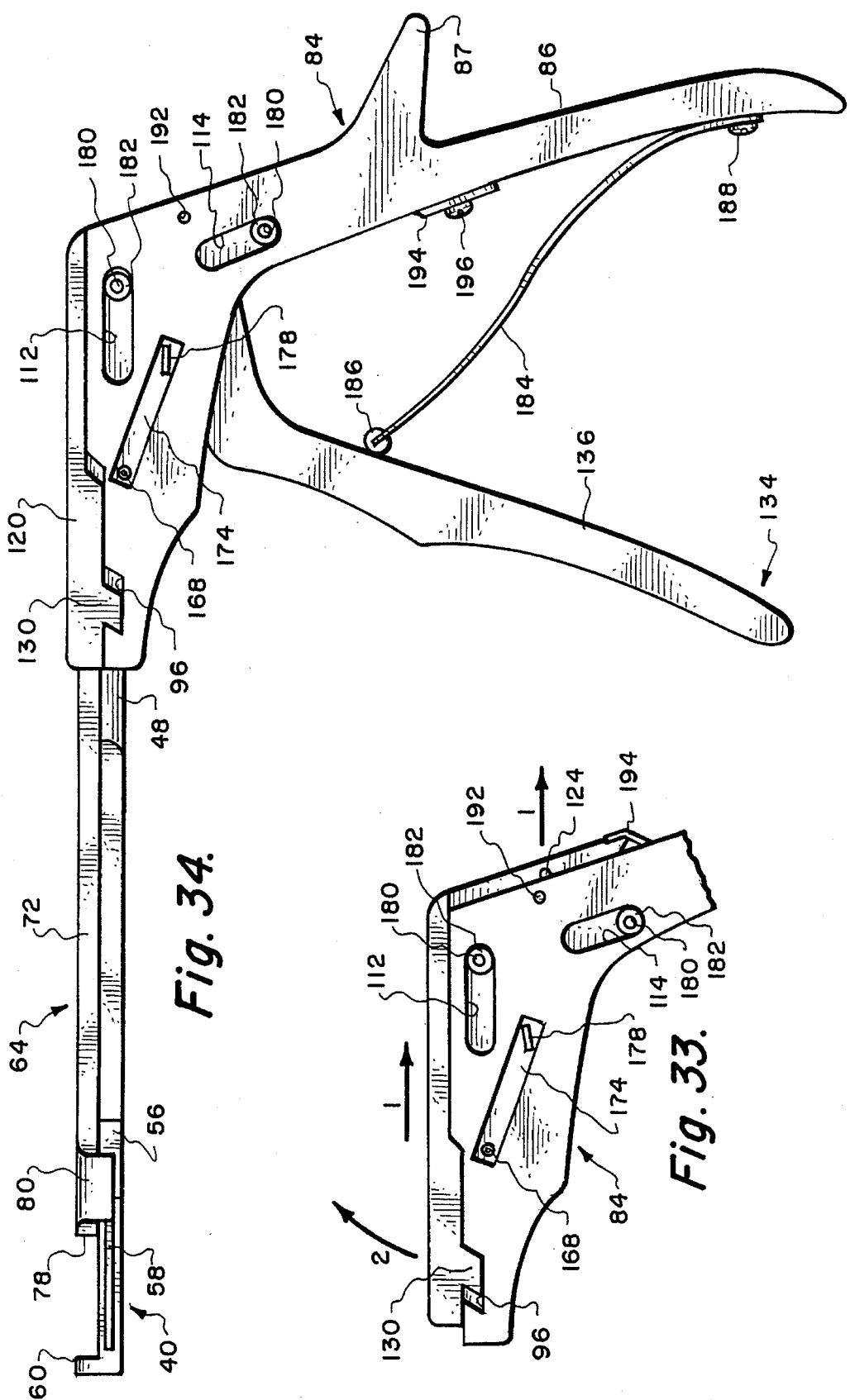

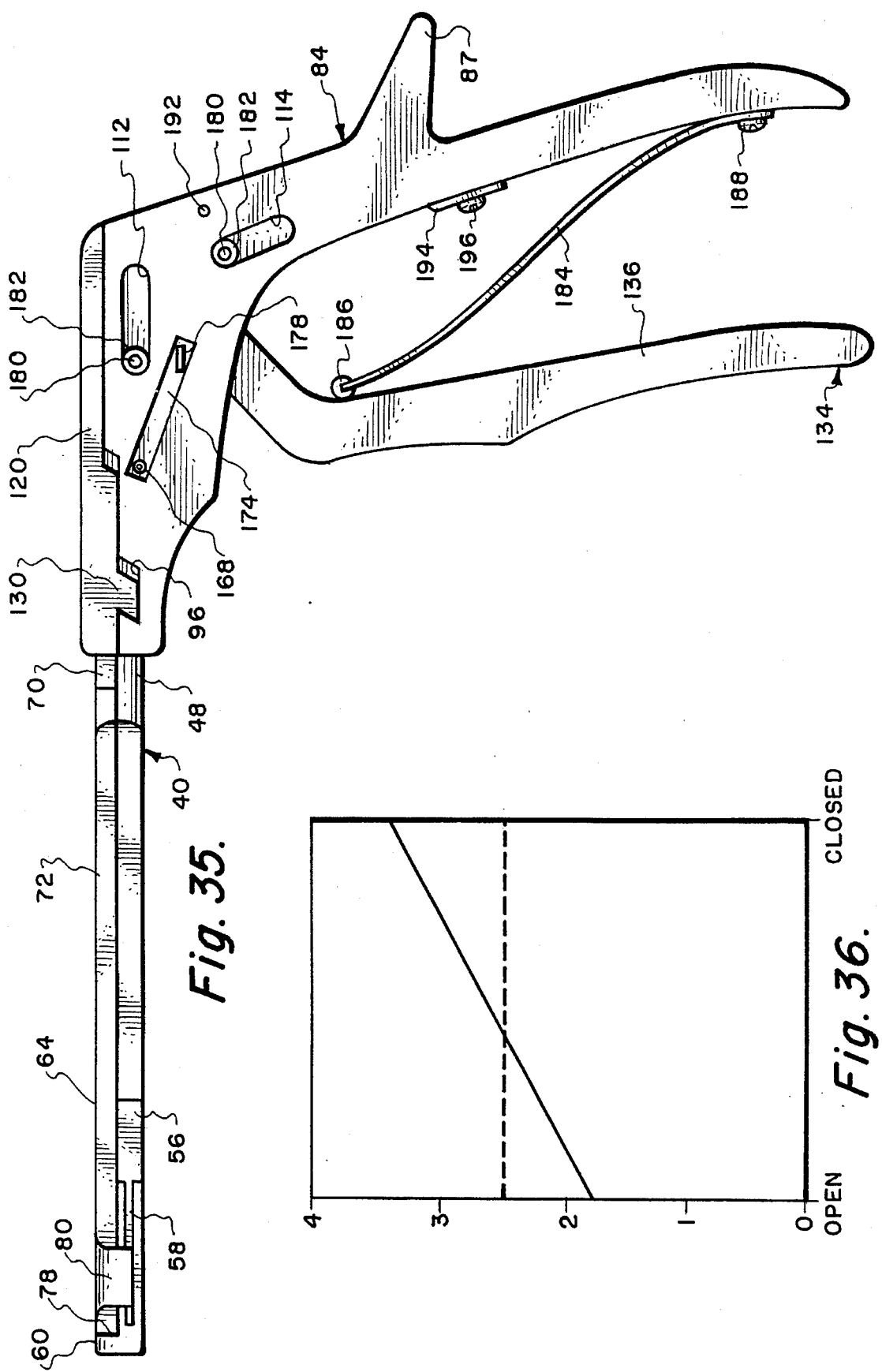

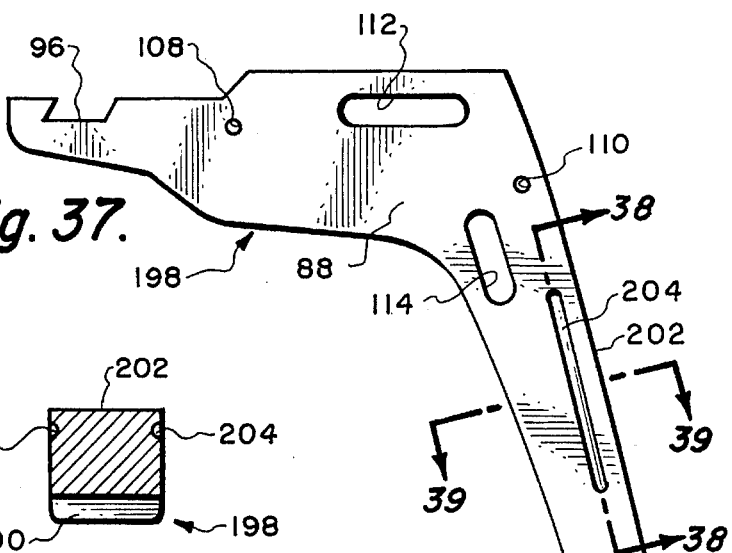
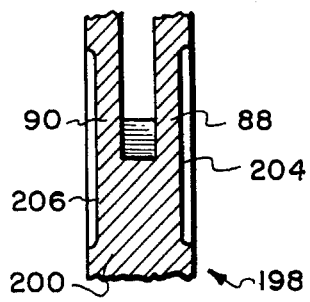
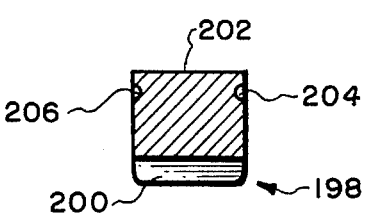
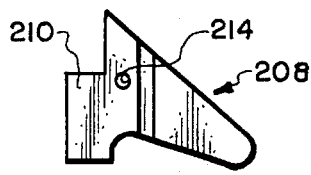
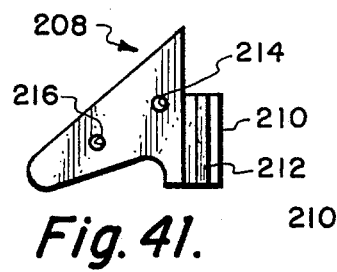
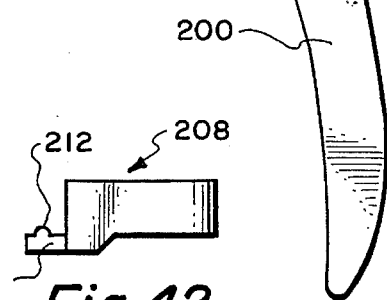
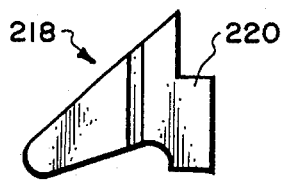
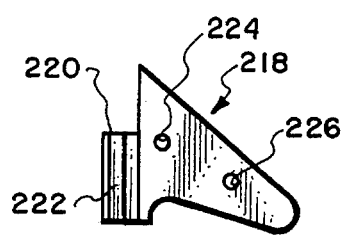
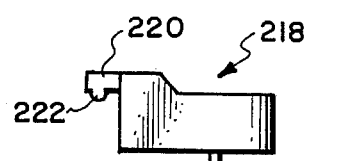

RONGEUR SURGICAL INSTRUMENT

This application is a continuation-in-part, of application Ser. No. 716,557, filed Jun. 17, 1991, now abandoned.

IDENTIFICATION OF RELATED PATENT APPLICATION

This application is related to a commonly owned patent application U.S. Ser. No. 7/608,659, which was filed on Nov. 2, 1990, entitled "Rongeur Surgical Instrument," which application is hereby incorporated herein by reference.

BACKGROUND OF THE INVENTION

1. Field of the Invention

The present invention relates generally to a rongeur surgical instrument, and more particularly to an improved rongeur surgical instrument having a trigger mechanism providing a variable mechanical advantage for operation of the cutting element in the instrument, and also having an improved shaft design which both maintains cutting edge alignment with the footplate anvil surface and provides a mechanism for preventing cut portions of body material from aggregating near the distal end of the shaft and interfering with the cutting operation.

In surgical procedures, having a properly designed instrument is crucial to allow the surgeon to optimize treatment for the patient. One such instrument used in certain procedures is a surgical instrument called a rongeur, which is a heavy-duty cutting forceps for removing small pieces of bone, cartilage, or other tough body tissue from small spaces in the human body. Rongeurs are typically used in conjunction with procedures on vertebrae of the back, as well as in procedures on the knee.

A rongeur typically includes an extended two-piece shaft supported at the proximal end by a grip which may be pistol-shaped. One of the shaft members is fixed with respect to the grip, and has a transversely mounted footplate mounted at its distal end. The other shaft member is moveable in reciprocating axial movement adjacent to the first shaft member, with the reciprocating movement being caused by squeezing of a triggering mechanism pivotally mounted with respect to the grip.

The distal end of the second shaft member is generally axially aligned with the footplate mounted on the first shaft member. The distal end of the second shaft member contains a cutting member positioned for engagement with the footplate when the second shaft member is in its most distal position. As the trigger is squeezed, the distal end of the second shaft member moves against the footplate, which acts as an anvil surface. By placing bone or tissue to be cut between the cutting member and the footplate and then squeezing the trigger, small segments of the bone or tissue may be removed with a high degree of precision.

It will at once be appreciated by those skilled in the art that since the areas in which a rongeur is used are small, the distal end of the shaft must by necessity be quite small. As such, the footplate must also be quite small and relatively thin. This brings conflicting design requirements into view. Since a surgeon using a rongeur will typically be cutting hard materials such as bone or cartilage, the forces present at the footplate and cutting member are quite large. The small sizes of the footplate and the cutting member, dictated by the small areas in which the rongeur must operate, make them susceptible to bending or misalignment.

The related patent application which was incorporated by reference above solves this problem by seeking to limit transverse movement of the distal end of the second shaft member with respect to the distal end of the first shaft member, and also by limiting the amount of force the surgeon may apply to the cutting member against the footplate. The limit on transverse movement of the second shaft member is provided by having inwardly extending tabs on side portions of the distal end of the second shaft member engaging slots in the side of the distal end of the first shaft member. This of course helps considerably, but with the application of sufficient force the side portions may actually be bent outwardly sufficiently to allow the tabs to escape engagement with the slots, allowing misalignment of the cutting member with respect to the footplate.

Thus, it is an objective of the present invention that it provide a more positive mechanism for maintaining the relative alignment of the cutting member and the footplate in a rongeur surgical instrument. It is also a further objective that the mechanism for maintaining alignment of the cutting member and the footplate not interfere in any way with the cutting operation of the surgical instrument, or with the surgeon's vision of the cutting operation. It is a related objective that this desirable design ambition be achieved without increasing the size of the members in any way, thereby maintaining a small distal shaft configuration.

Another area for improvement is in the actuation of the trigger member to move the cutting member into engagement with the footplate. Every rongeur design in the past has used a linear trigger member and constant linear actuation of the cutting member. Thus, movement of the trigger member in a first amount will always cause movement of the cutting member in a second amount. It would be advantageous for movement of the trigger member to cause a greater degree of movement of the cutting member prior to engagement of bone or tissue, when less precision of movement, as well as less of a mechanical advantage, is required. Upon engagement of the bone or tissue between the cutting member and the footplate, it would then be advantageous for movement of the trigger member to cause a lesser degree of movement of the cutting member, when greater precision of movement, as well as more of a mechanical advantage, is required.

It is accordingly a primary objective of the present invention to provide a variable degree of mechanical advantage to the trigger-actuated operation of the movement of the cutting member toward the footplate. During initial actuation of the trigger member to initiate movement of the cutting member toward the footplate prior to engagement of bone or tissue, it is thus an objective to provide a lesser degree of mechanical advantage, together with a greater degree of movement of the cutting member. In contrast, during actuation of the trigger subsequent to engagement of bone or tissue between the cutting member and the footplate, it is an objective to provide a greater degree of mechanical advantage, together with a lesser degree of movement of the cutting member.

Another problem encountered in operation of a rongeur is the aggregation of bone or tissue chips previously cut in the cutting area, where they can interfere with the engagement of additional portions of bone or tissue to be cut. The cutting member at the distal end of the second shaft member may have a tunnel therein, as disclosed in the related patent application which was incorporated by reference above. This tunnel is designed to allow bone and tissue chips to be carried proximally away from the footplate and out of the path of the cutting member. However, what typically happens is that the reciprocating movement of the second shaft member with respect to the first shaft member causes bone and tissue chips to move distally out of the tunnel (during movement of the second shaft member in a proximal direction), and to inhibit future cutting operations of the rongeur by their presence between the cutting member and the footplate.

It is thus also a primary objective of the present invention that it provide a mechanism for inhibiting movement of bone or tissue chips, once cut, distally out of the tunnel in the cutting member. This mechanism should thus provide a restriction on the movement of the bone or tissue chips, but without restricting in any way the cutting operation of the surgical instrument. Thus, the mechanism for inhibiting movement of bone or tissue chips to the location of the cutting operation should enhance the ease of the cutting operation by not requiring the surgeon to pause to remove bone or tissue chips from the cutting members.

A further problem of the rongeur surgical instruments presently available is that they have a grip which is designed to fit an "average" size hand. Since the size of surgeons' hands may vary substantially, it may be seen that the fit of the grip of such known rongeurs represents a compromise, fitting only an "average" size hand well. For those surgeons having hands which are either larger or smaller than average, the fit of the grip of such rongeurs will be something less than ideal.

It is thus yet another objective of the rongeur surgical instrument of the present invention that it provide a grip which is adjustable to provide a custom fit to a wide variety of hand sizes. The variable fit of the grip should be capable of being modified to provide a comfortable accommodation for any hand size through a simple adjustment which may be quickly accomplished. It is an additional objective of the rongeur surgical instrument of the present invention that it be of solid construction, to be both durable and long-lasting in operation. Finally, it is also an objective that all of the aforesaid advantages and objectives of the present invention be achieved without incurring any substantial relative disadvantage.

SUMMARY OF THE INVENTION

The disadvantages and limitations of the background art discussed above are overcome by the present invention. With this invention, an improved rongeur surgical instrument is described which offers significant advantages in both construction and operation over previously known rongeur designs. The basic configuration of the rongeur is similar to the related patent application which was incorporated by reference above, having a pistol-shaped configuration with a removable two-piece shaft. Beyond this similarity, there are several differences in the construction and operation of the shaft members, the trigger-operated actuating mechanism, and the members used to support the distal end of the shaft.

Beginning with the shaft, there are two key differences which result in substantial improvements in the operation of the rongeur surgical instrument of the present invention. First, there are a plurality of grooves in the top surface of the first shaft member, which is the surface upon which the second shaft member reciprocates. The tunnel in which bone and tissue chips previously cut will be located is defined between the inverted U-shape of the cutting member at the distal end of the second shaft member, and this top surface of the first shaft member. The grooves are located on the first shaft member to be within the tunnel when the second shaft member is in its proximal position (by nature of the trigger member having been released and not currently being squeezed).

The grooves are configured to allow movement of the bone and tissue chips past them in a proximal direction, but to resist movement of the bone and tissue chips in a distal direction. It will be appreciated by those skilled in the art that the bone and tissue chips, once cut, tend to stay within the tunnel inside the distal portion of the second shaft member, being forced distally out by repeated movement of the second shaft member in a proximal direction and the friction of the first shaft member. The grooves prevent the bone and tissue chips from this distal movement relative to the second shaft member; in fact, the grooves tend to force the bone and tissue chips further proximally in the second shaft member.

Another difference between the construction of the shaft of the rongeur surgical instrument of the present invention and the rongeur disclosed in the related patent application which was incorporated by reference above is that the tabs on the second shaft member and the grooves in the first shaft member which the tabs engage are arranged and configured to prevent the tabs from moving outwardly from engagement with the grooves. Thus, even under heavy loading conditions, the alignment of the distal portions of the shaft members is preserved, preventing misalignment of the cutting member and the footplate. The modification does not change the overall outer dimensions of the shaft members, thus presenting an improved construction with no increase in size which could make the instrument more difficult to use.

Referring now to the rest of the instrument from which the shaft extends, a housing member is provided which has a pistol-shaped grip extending therefrom. The top of the housing member is open, with a pivotally mounted cover member supported at the rear of the housing member. The cover member is opened by pulling it back to disengage a latching mechanism, and then pivoting it up and toward the back. The distal end of the shaft is supported between the top front portions of the housing and the cover member. The shaft has a plurality of rotational positions into which it may be placed (without opening the cover member) by actuating an ambidextrous release mechanism.

The trigger mechanism is actuated by squeezing a trigger member appearing similar to the trigger member of the rongeur disclosed in the related patent application which was incorporated by reference above. However, the trigger mechanism of the present invention is markedly different in operation, in that the pivot point of the trigger mechanism varies as the trigger member is squeezed. Thus, as the trigger member moves through its entire stroke, the pivot point continuously changes to utilize a progressively smaller lever arm.

The result of this is that the relative movement of the cutting member is not a constant linear function of the movement of the trigger member. Instead, as the trigger member is squeezed, the cutting member initially moves faster than in prior rongeurs, and then slower as the more precise part of the operation involving cutting of bone or tissue occurs. In addition, the torque progressively increases as the mechanical advantage increases throughout the stroke of the trigger member. Thus, maximum force and precision are presented when they are needed, near the end of the stroke of the trigger member. The overall operation is improved to a point previously unknown in the art, even in the state-of-the-art rongeur disclosed in the related patent application which was incorporated by reference above.

In addition, in an alternate embodiment, the grip includes a moveable spur to allow the grip to accommodate different hand sizes. The spur may be slid up and down the rear of the grip into a desired position, at which point it is fixed in place.

It may therefore be seen that the present invention teaches a more positive mechanism for maintaining the relative alignment of the cutting member and the footplate in a rongeur surgical instrument. The mechanism for maintaining alignment of the cutting member and the footplate does not interfere in any way with the cutting operation of the surgical instrument, or with the surgeon's vision of the cutting operation. In addition, this desirable design ambition is achieved without- increasing the size of the members in any way, thereby maintaining a small distal shaft configuration.

In another primary aspect, the present invention provides a variable degree of mechanical advantage to the trigger-actuated operation of the movement of the cutting member toward the footplate. During initial actuation of the trigger member to initiate movement of the cutting member toward the footplate prior to engagement of bone or tissue, the improved rongeur surgical instrument provides a lesser degree of mechanical advantage, together with a greater degree of movement of the cutting member. In contrast, during actuation of the trigger subsequent to engagement of bone or tissue between the cutting member and the footplate, the improved rongeur surgical instrument provides a greater degree of mechanical advantage, together with a lesser degree of movement of the cutting member.

In still another primary aspect, the present invention provides a mechanism for inhibiting movement of bone or tissue chips, once cut, distally out of the tunnel in the cutting member. This mechanism thus provides a restriction on the movement of the bone or tissue chips, but without restricting in any way the cutting operation of the surgical instrument. Thus, the mechanism for inhibiting movement of bone or tissue chips to the location of the cutting operation should enhance the ease of the cutting operation by not requiring the surgeon to pause to remove bone or tissue chips from the cutting members.

The rongeur surgical instrument of the present invention also provides a grip which is adjustable to provide a custom fit to a wide variety of hand sizes. The variable fit of the grip may be modified to provide a comfortable accommodation for any hand size through a simple adjustment which may be quickly and easily accomplished. The improved rongeur surgical instrument of the present invention is of solid construction, to be both durable and long-lasting in operation. Finally, all of the aforesaid advantages and objectives of the present invention are achieved without incurring any substantial relative disadvantage.

DESCRIPTION OF THE DRAWINGS

These and other advantages of the present invention are best understood with reference to the drawings, in which:

FIG. 10 is an end view of the second shaft member illustrated in FIGS. 7 through 9 from the distal end thereof, showing the configuration of the tabs which will extend into the slots in the sides of the first shaft member illustrated in FIG. 6;

FIG. 11 is a side view of the second shaft member of FIGS. 7 through 10 positioned above the first shaft member of FIGS. 1 through 6 with a relative longitudinal position in which the second shaft member may be installed onto first shaft member;

FIG. 12 is a side view similar to FIG. 11, but with the second shaft member installed on the first shaft member, showing the second shaft member is its first or proximal position relative to the first shaft member;

FIG. 13 is a side view of the first and second shaft members similar to FIG. 12, showing the second shaft member is its second or distal position relative to the first shaft member, with the cutting member engaging the footplate;

FIG. 14 is a side plan view of a housing member, showing a pistol-shaped grip and two grooves by which a trigger member will be mounted for movement about a variable pivot point;

FIG. 15 is a top view of the housing member illustrated in FIG. 14, showing the location in which the wheel member at the proximal end of the first shaft member illustrated in FIG. 6 will be installed, and also showing the location of various grooves and recesses within the housing member;

FIG. 16 is a cross-sectional view of the housing member illustrated in FIGS. 14 and 15, showing the location of various grooves in the interior of the housing member;

FIG. 17 is a cross-sectional view of the housing member illustrated in FIGS. 14 through 16 at the location in which the wheel member at the proximal end of the first shaft member illustrated in FIG. 6 will be installed;

FIG. 18 is a cross-sectional view of the housing member illustrated in FIGS. 14 through 17 at the location in which two grooves intersect;

FIG. 19 is a side plan view of a cover member for installation on top of the housing member illustrated in FIGS. 14 through 18, showing the location of a slotted aperture which will allow limited rearward movement of the cover member to disengage its locking mechanism from the housing member to allow the cover member to be opened;

FIG. 20 is a bottom plan view of the cover member illustrated in FIG. 19, showing the location in which the wheel member at the proximal end of the first shaft member illustrated in FIG. 6 will be located;

FIG. 21 is a cross-sectional view of the cover member illustrated in FIGS. 19 and 20;

FIG. 28 is a side plan view of a locking member used to selectively inhibit rotation of the wheel member at the proximal end of the first shaft member illustrated in FIG. 6;

FIG. 29 is a front view of the locking member illustrated in FIG. 28;

FIG. 30 is a plan view of a pin used with the locking member illustrated in FIGS. 28 and 29, showing the location of sets of ridges on the pin used for frictional engagement, the center one of which sets of ridges is used to engage an aperture in the locking member;

FIG. 31 is a lever used for operating the locking member illustrated in FIGS. 28 and 29, via the pin illustrated in FIG. 30;

FIG. 32 is a partially cutaway view of the housing member illustrated in FIGS. 14 through 18, with the cover member illustrated in FIGS. 19 through 21, the trigger member illustrated in FIGS. 22 and 23, the slide member illustrated in FIGS. 24 through 27, the locking member illustrated in FIGS. 28 and 29, and the pin illustrated in FIG. 30 installed in the housing member;

FIG. 33 is a partial side view of the assembly illustrated in FIG. 32, with the cover member moved rearwardly to disengage the latching mechanism to allow the cover member to be opened;

FIG. 34 is a plan view of the rongeur surgical instrument of the present invention, consisting of the assembly illustrated in FIG. 32, with the first and second shaft members as illustrated in FIG. 12 and 13 installed, with the trigger member in the unsqueezed position, and the second shaft member is its first or proximal position relative to the first shaft member;

FIG. 35 is a plan view of the rongeur surgical instrument of the present invention shown in FIG. 34, with the trigger member in the squeezed position, and the second shaft member is its second or distal position relative to the first shaft member, with the cutting member engaging the footplate;

FIG. 36 is a plot of mechanical advantage versus position of the cutting member relative to the footplate, with operation of a conventional rongeur being shown by a dotted line, and operation of the improved rongeur surgical instrument of the present invention being shown by a solid line;

FIG. 37 is a side plan view of an alternate embodiment housing member, showing a pistol-shaped grip having no spur member extending from the rear of the grip portion thereof, and also showing one of two grooves in the grip portion;

FIG. 38 is a first cross-sectional view of the alternate embodiment housing member illustrated in FIG. 38, showing the location of both grooves in the grip portion;

FIG. 39 is a second cross-sectional view of the alternate embodiment housing member illustrated in FIGS. 37 and 38, showing both grooves in the grip portion in cross-section;

FIG. 40 is a left side plan view of a left adjustable spur half showing an arm extending from the lower left front portion thereof;

FIG. 41 is a right side plan view of the left adjustable spur half illustrated in FIG. 40, showing the location of a tab extending from the right side of the arm;

FIG. 42 is a top view of the left adjustable spur half illustrated in FIGS. 40 and 41, showing the cross-sectional configuration of the tab;

FIG. 43 is a right side plan view of a right adjustable spur half showing an arm extending from the lower right front portion thereof;

FIG. 44 is a left side plan view of the right adjustable spur half illustrated in FIG. 43, showing the location of a tab extending from the left side of the arm;

FIG. 45 is a top view of the right adjustable spur half illustrated in FIGS. 43 and 44, showing the cross-sectional configuration of the tab;

DETAILED DESCRIPTION OF THE PREFERRED EMBODIMENT

The preferred embodiment of the present invention has improvements embodied in the construction and operation of both the shaft members and the mounting and actuating mechanism. The description of the design and operational details will focus first on the shaft members, then on the mounting and actuating mechanism in and of itself, and finally on the operation of the improved rongeur surgical instrument as a whole.

Figure 1:
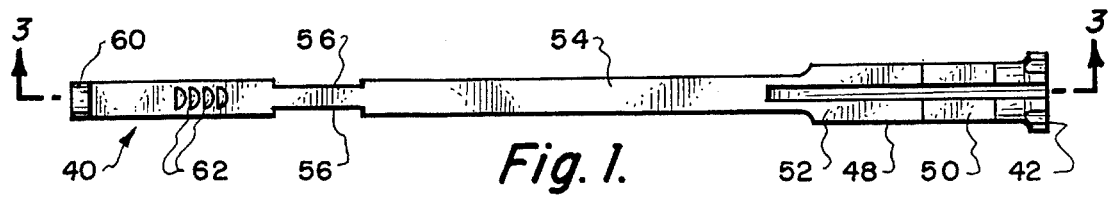
FIG. 1 is a top plan view of a first shaft member for the rongeur surgical instrument of the present invention, showing the placement and configuration of grooves used to inhibit distal movement of bone and tissue chips while allowing their proximal movement.
Figure 2:
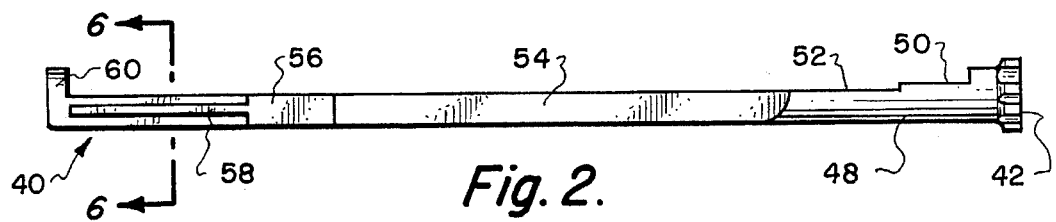
FIG. 2 is a side view of the first shaft member illustrated in FIG. 1, showing in profile a transversely mounted footplate, and also showing a slot located on the side of the first shaft member near the distal end thereof.
Figure 3:
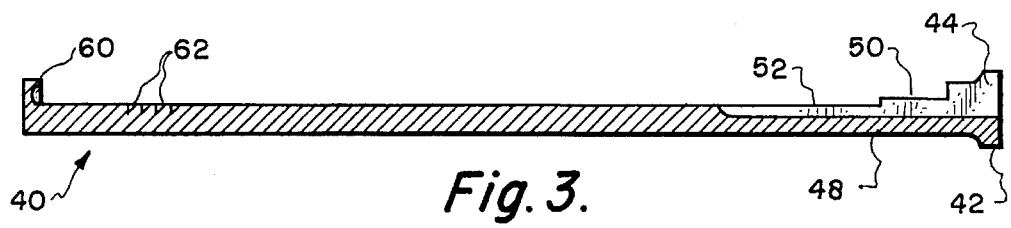
FIG. 3 is a cross-sectional view of the first shaft member illustrated in FIGS. 1 and 2, showing the cross-sectional configuration of the grooves.

Referring first to FIGS. 1 through 6, a first shaft member 40 is illustrated. The first shaft member 40 as shown in FIGS. 1 through 3 has a proximal end on the right side of the drawings, and a distal end on the left side of the drawings. It is the distal end which will be the working end of the rongeur surgical instrument of the present invention.

Figure 5:
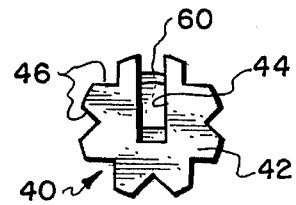
FIG. 5 is an end view of the first shaft member illustrated in FIGS. 1 through 4 from the proximal end thereof, showing the configuration of a wheel member having grooves therein to facilitate various rotational alignments of the first shaft member and a second shaft member mounted on the first shaft member.

The proximal end of the first shaft member 40 is a wheel member 42 which is essentially round with a plurality of notches therein. The longitudinal axis of the first shaft member 40 is essentially perpendicular to the wheel member 42. With the exception of a rectangular notch 44 in the top of the wheel member 42, there are triangular notches 46 located at evenly spaced increments around the outer periphery of the wheel member 42. The rectangular notch 44 extends much further into the wheel member 42 (over half way through, as shown in FIGS. 3 and 5) than do the triangular notches 46.

In the preferred embodiment illustrated, there are seven of the triangular notches 46 in addition to the rectangular notch 44, with 45 degrees between each adjacent pair of the notches 44 or 46. The notches 44 and 46 will be used to position the first shaft member 40 with respect to a housing member to be discussed below in a desired rotational position in 45 degree increments. It will be apparent to those skilled in the art that more or fewer of the triangular notches 46 could be used if desired.

Extending distally from the wheel member 42 is a cylindrical segment 48 which has a diameter smaller than the diameter of the wheel member 42. The cylindrical segment 48 has three distinct portions therein, all having the same diameter, and all having the rectangular notch 44 extending therein at the same depth as in the wheel member 42. The first portion of the cylindrical segment 48 is immediately distal to the wheel member 42, and is completely cylindrical except for the rectangular notch 44 therein.

The second portion of the cylindrical segment 48, which is immediately distal to the first portion, has a flat surface 50 on the top side thereof, with the balance of the cylindrical material removed. Immediately distal to the second portion of the cylindrical segment 48 is a third portion, which has a flat surface 52 on the top side thereof. The flat surface 52 is lower than the flat surface 50, with the third portion of the cylindrical segment 48 having even more material removed from the top of the cylinder.

Figure 4:
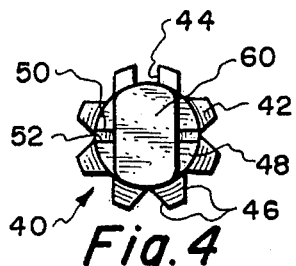
FIG. 4 is an end view of the first shaft member illustrated in FIGS. 1 through 3 from the distal end thereof, showing the configuration of the footplate.

Located immediately distal to the third portion of the cylindrical segment 48 is a long bottom shaft 54 which extends to the distal end of the first shaft member 40. The long bottom shaft 54 has a flat top surface which is coplanar with the flat surface 52 of the cylindrical segment 48. Note that the rectangular notch 44 extends only into a short proximal portion of the long bottom shaft 54. The long bottom shaft 54 is narrower than the width of the cylindrical segment 48, as best seen in FIG. 4. For most of its length, the long bottom shaft 54 has a rounded bottom edge and flat side walls, as best seen in FIG. 4.

Located about two-thirds of the way from the proximal end of the long bottom shaft 54 toward the distal end thereof both sides of the long bottom shaft 54 are machined inwardly at 56, as best shown in FIG. 1. These inwardly machined portions 56 are to allow retaining mechanisms located on a second shaft member to be discussed in conjunction with FIGS. 7 through 10 to be installed on the first shaft member 40.

Figure 6:
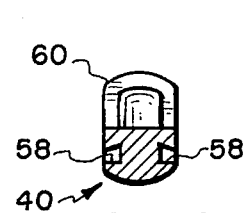
FIG. 6 is a cross-sectional view of the first shaft member illustrated in FIGS. 1 through 5, showing the configuration of the slots in the sides of the first shaft member.

Located in both sides of the long bottom shaft 54 distally from the inwardly machined portions 56 nearly to the distal end of the long bottom shaft 54 are two slots 58. The configuration of the slots 58 are different from the slots used in the related patent application which was incorporated by reference above. The slots 58 thus extend longitudinally, and in cross-section as shown in FIG. 6 widen as they extend into the sides of the long bottom shaft 54. The narrowest portion of the slots 58 is thus adjacent the outside of the long bottom shaft 54.

Located at the distal end of the long bottom shaft 54 is a footplate 60, which extends transversely from the top of the long bottom shaft 54. In FIGS. 2, 3, and 6, the footplate 60 extends orthogonally to the flat top surface of the long bottom shaft 54. However, in other embodiments, the footplate 60 could be located at an angle, typically with the footplate 60 declining away from the proximal end of the first shaft member 40. For example, the footplate 60 may be mounted at a 45 degree angle declining away from the proximal end of the first shaft member 40. Note that as shown in FIG. 3, the side of the footplate 60 facing proximally has a recess therein, to better enable the footplate 60 to act as an anvil in conjunction with a cutting member to be discussed below in conjunction with FIGS. 7 through 10.

Located in the top surface of the long bottom shaft 54 spaced slightly proximally of the footplate 60 are a plurality of grooves 62. As those skilled in the art know, bone or tissue chips, once removed by the operation of the rongeur, will be located in a tunnel defined in part by the top surface of the long bottom shaft 54. As stated above, it is desirable to provide a mechanism allowing such bone and tissue chips to move proximally with respect to the first shaft member 40, while inhibiting distal movement. The grooves 62 are this mechanism.

The grooves 62 are configured so that the edge of each of the grooves 62 closest to the proximal end of the first shaft member 40 are tapered to facilitate the movement of bone or tissue chips in the proximal direction. However, the edge of each of the grooves 62 closest to the distal end of the first shaft member 40 are essentially orthogonal to the flat top surface of the long bottom shaft 54. This configuration will impede the movement of bone or tissue chips in the distal direction. If desired, the sides of the grooves 62 closest to the distal end of the first shaft member 40 could even be undercut slightly to provide a sharper retaining edge.

Figure 7:
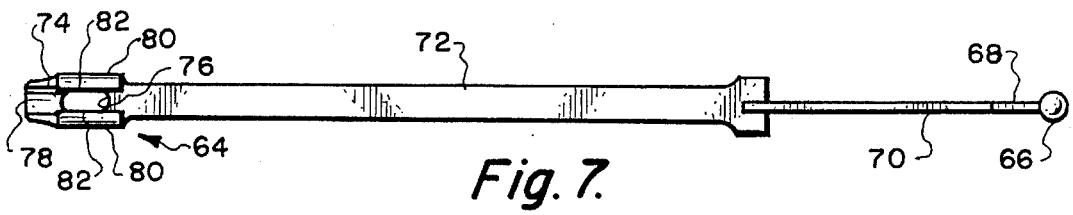
FIG. 7 is a bottom plan view of a second shaft member for mounting for reciprocating movement on top of the first shaft member shown in FIGS. 1 through 6, showing the cutting member at the distal end of the second shaft member, a ball located at the distal end of the second shaft member for driving the reciprocating movement of the second shaft member, and the placement of an aperture in the top side of the second shaft member near the distal end thereof.
Figure 8:
FIG. 8 is a side view of the second shaft member illustrated in FIG. 7.
Figure 9:
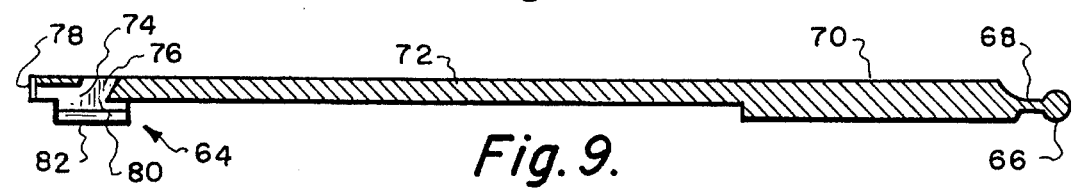
FIG. 9 is a cross-sectional view of the second shaft member illustrated in FIGS. 7 and 8, showing the tunnel inside the distal end of the second shaft member adjacent the cutting member, and the communication of the tunnel with the aperture in the top of the second shaft member.

Referring next to FIGS. 7 through 10, a second shaft member 64 is illustrated. The second shaft member 64 as shown in FIGS. 7 through 9 has a proximal end on the right side of the drawings, and a distal end on the left side of the drawings. Again, it is the distal end which will be the working end of the rongeur surgical instrument of the present invention.

The second shaft member 64 has a ball 66 located at the proximal end thereof, which ball 66 will be used to drive the second shaft member 64 in reciprocating motion. The ball 66 is connected to a short shaft 68, which in turn is connected to a long flat rectangular plate 70. The flat rectangular plate 70 is oriented in a vertical manner, and has a thickness to allow the flat rectangular plate 70 to fit slideably into the rectangular notch 44 in the first shaft member 40 (FIG. 1).

A long top shaft 72 which is attached to the distal end of the flat rectangular plate 70 extends essentially to the distal end of the second shaft member 64. The long top shaft 72 has a flat bottom surface, and is of approximately the same width as the width of the long bottom shaft 54 of the first shaft member 40 (FIG. 1). For most of its length, the second shaft member 64 has a rounded top edge and flat side walls. In the preferred embodiment, the extreme proximal end of the second shaft member 64 has a wider diameter similar to the diameter of the cylindrical segment 48 of the first shaft member 40 (FIG. 1).

The distal end of the long top shaft 72 is hollow to form a tunnel 74 therein, as best shown in FIG. 9 (the bottom of the tunnel 74 will be defined by the top surface of the long bottom shaft 54 of the first shaft member 40 shown in FIGS. 1 and 2). The distal end of the tunnel 74 is open, with the extreme distal portion of the long top shaft 72 being U-shaped in cross-section, as best shown in FIG. 10. The proximal end of the tunnel 74 communicates with an aperture 76 located in the top of the long top shaft 72.

The distal end of the long top shaft 72 is sharpened to form a cutting member 78. It is this sharp-edged cutting member 78 which will be driven into engagement with the footplate 60 of the first shaft member 40 (FIGS. 1 through 3) to cut bone or tissue. Thus, it will be appreciated that the relative sizes and configurations of the cutting member 78 and the footplate 60 are directly related. For example, if the footplate 60 is mounted at a 45 degree angle declining away from the proximal end of the first shaft member 40, the cutting member 78 would have a similar orientation.

Located on the sides of the long top shaft 72 of the second shaft member 64 near the distal end thereof are two side members 80 which extend below the flat bottom side of the long top shaft 72. The side members 80 are designed to fit over the side of the long bottom shaft 54 of the first shaft member 40 (FIG. 1).

On the facing inner sides of each of the side members 80 near the bottoms thereof is an inwardly extending tab 82. The configuration of the inwardly extending tabs 82 are different from the tabs used in the related patent application which was incorporated by reference above. The inwardly extending tabs 82 extend longitudinally, and in cross-section as shown in FIG. 10 they widen as they extend inwardly. The narrowest portion of the inwardly extending tabs 82 is thus immediately adjacent the side members 80. The inwardly extending tabs 82 are designed for engagement with the slots 58 in the first shaft member 40 (FIGS. 2 and 6).

Referring now to FIGS. 11, 12, and 13, the assembly of the second shaft member 64 onto the first shaft member 40 is illustrated. In FIG. 11, the second shaft member 64 is illustrated above the first shaft member 40 in the proper manner for assembly. The inwardly extending tabs 82 on the side members 80 of the second shaft member 64 must be directly above the inwardly machined portions 56 on the sides of the first shaft member 40. The flat rectangular plate 70 of the second shaft member 64 must also be above the rectangular notch 44 in the first shaft member 40. The second shaft member 64 may then be lowered onto the first shaft member 40, with the inwardly extending tabs 82 fitting around the inwardly machined portions 56, and the flat rectangular plate 70 fitting into the rectangular notch 44.

FIG. 12 shows the second shaft member 64 installed onto the first shaft member 40 in this manner, with the inwardly extending tabs 82 on the side members 80 of the second shaft member 64 engaged in the slots 58 in the first shaft member 40. The flat rectangular plate 70 of the second shaft member 64 is also engaged in the rectangular notch 44 of the first shaft member 40. Note that in the position shown in FIG. 12, the distal end of the long top shaft 72 is in its fully proximal position on the flat surface 52 of the first shaft member 40. Further proximal movement of the second shaft member 64 without first lifting its proximal end will thus be prevented.

FIG. 13 illustrates the second shaft member 64 in its fully distal position on the first shaft member 40. It may be seen that in this position, the cutting member 78 of the second shaft member 64 has engaged the footplate 60 of the first shaft member 40. It will thus be apparent to those skilled in the art that the second shaft member 64 will reciprocate between the positions shown in FIGS. 12 and 13 in operation.

Note that the cutting member 78 of the second shaft member 64 will always be maintained in alignment with the footplate 60 of the first shaft member 40, due to the interlocking design of the inwardly extending tabs 82 of the second shaft member 64 and the slots 58 of the first shaft member 40. Thus, the inwardly extending tabs 82 can no longer pull radially out of the slots 58.

Note also the tunnel 74 in the second shaft member 64 (FIG. 9) and above the top surface of the long bottom shaft 54 of the first shaft member 40 will move in reciprocating fashion over the grooves 62 in the first shaft member 40. Thus, the grooves 62 will act to prevent bone and tissue chips from being moved distally out of the distal end of the second shaft member 64 by the reciprocating movement of the second shaft member 64 on the first shaft member 40. This completes the description of the shaft members 40 and 64 of the rongeur surgical instrument of the present invention.

Referring next to FIGS. 14 through 18, a housing member 84 is illustrated which is basically pistol-shaped. The housing member 84 has a grip portion 86 extending from the bottom and rear thereof. A spur member 87 extends rearwardly from the grip portion 86 at the rear and near the top thereof to provide support for the hand of a user (not shown). The housing member 84 is open on the top side thereof, as best shown in FIG. 15. The rear half of the top of the housing member 84 is open between the left and right side walls 88 and 90 of the housing member 84, with the interior of the housing member 84 being both hollow and open to the bottom at the front of the grip portion 86, as best shown in FIG. 16.

Located in the top side of the housing member 84 near the front is a cylindrical recess 92, which will receive the bottom portion of the cylindrical segment 48 of the first shaft member 40 (FIG. 2). Immediately to the rear of the cylindrical recess 92 in the housing member 84 is a larger diameter cylindrical recess 94, which is for receiving the wheel member 42 of the first shaft member 40 (FIG. 2). The cylindrical recess 94 is of a length to admit the wheel member 42 without allowing the first shaft member 40 to move in an axial direction.

Located on each side of the housing member 84 at the top and around the cylindrical recess 92 is a notch 96, best shown in profile in FIGS. 14 and 16. The notches 96 are parallelogram-shaped, with the sides being angled upward and backward. This configuration of the notches 96 is for a latching mechanism which will be discussed below in conjunction with FIG. 32.

Located in the top of the housing member 84 immediately to the rear of and concentric with the cylindrical recess 94 is a smaller diameter cylindrical recess 98. Extending downwardly from the bottoms of both of the cylindrical recesses 94 and 98 is a notch 100. The notch 100, which is narrower than the diameter of the cylindrical recess 98, is open at the rear thereof to the space between the left and right side walls 88 and 90. Located at the bottom of the notch beneath the cylindrical recess 94 is a small vertically oriented cylindrical recess 102.

Located immediately to the rear of the cylindrical recess 98 and the notch 100 are two vertical slots 104. One of the vertical slots 104 is located in the interior of the left side wall 88, and the other of the vertical slots 104 is located in the interior of the right side wall 90. The vertical slots 104 are open at the top of the housing member 84, and extend about halfway down the interiors of the left and right side walls 88 and 90.

Located at the bottom of the vertical slots 104 and extending rearwardly are two horizontal slots 106. One of the horizontal slots 106 is located in the interior of the left side wall 88, and the other of the horizontal slots 106 is located in the interior of the right side wall 90. The fronts of the horizontal slots 106 are thus in communication with the bottoms of the vertical slots 104. The horizontal slots 106 extend rearwardly, but do not extend to the rear of the left and right side walls 88 and 90.

Located laterally in the housing member 84 are axially aligned apertures 108 which extend through the vertical slots 104 at intermediate positions therein. Located near the rear of the housing member 84 at a level just below the horizontal slots 106 are two axially aligned apertures 110 which also extend laterally through the left and right side walls 88 and 90 of the housing member 84.

Located in each of the left and right side walls 88 and 90 of the housing member 84 are two pairs of slots 112 and 114. One of the slots 112 is horizontally located just below the top of the housing member 84 in each of the left and right side walls 88 and 90. The slots 114 are located in the left and right side walls 88 and 90 above the front of the grip portion 86, and extend upward and slightly toward the front of the housing member 84. All of the slots 112 and 114 extend through the left and right side walls 88 and 90 of the housing member 84.

Located in the front of the grip portion 86 near the bottom thereof is a threaded aperture 116. Located nearer the top of the grip portion 86 is another threaded aperture 118.

Referring now to FIGS. 19 through 21, a cover member 120 for enclosing the top of the housing member 84 (FIG. 15) is illustrated. The cover member 120 is mounted on a support arm 122, which extends downwardly from the rear of the cover member 120. The support arm 122 is of a width (FIG. 20) to fit between the left and right side walls 88 and 90 of the housing member 84. Extending laterally through the support arm 122 is a horizontally disposed slot 124, which will be used to mount the cover member 120 onto the housing member 84.

Located in the bottom side of the cover member 120 at the front is a cylindrical recess 126 for receiving the cylindrical segment 48 of the first shaft member 40 (FIG. 2). Located to the rear of the cylindrical recess 126 is a larger diameter cylindrical recess 128, which is for receiving the wheel member 42 of the first shaft member 40 (FIG. 2). The cylindrical recess 128 is of a length to admit the wheel member 42, and also to allow the cover member 120 to move rearwardly slightly to allow the cover member 120 to be unlatched, as will become evident in the discussion of FIG. 32.

Located on each side of the cover member 120 at the bottom and around the cylindrical recess 126 is a tab 130, best shown in profile in FIGS. 19 and 21. The tabs 130 are essentially parallelogram-shaped (with rounded lower corners), with the sides being angled downward and forward. The tabs 130 are not as long as are the notches 96 in the housing member 84 (FIGS. 14 and 16). This configuration of the tabs 130 is for a latching mechanism which, as mentioned above, will be discussed below in conjunction with FIG. 32.

Located to the rear of the cylindrical recess 128 in the cover member 120 is a smaller cylindrical recess 132. Behind this cylindrical recess 132, the cover member 120 is thinner, designed to cover the top of the rear portion of the housing member 84.

Figure 22:
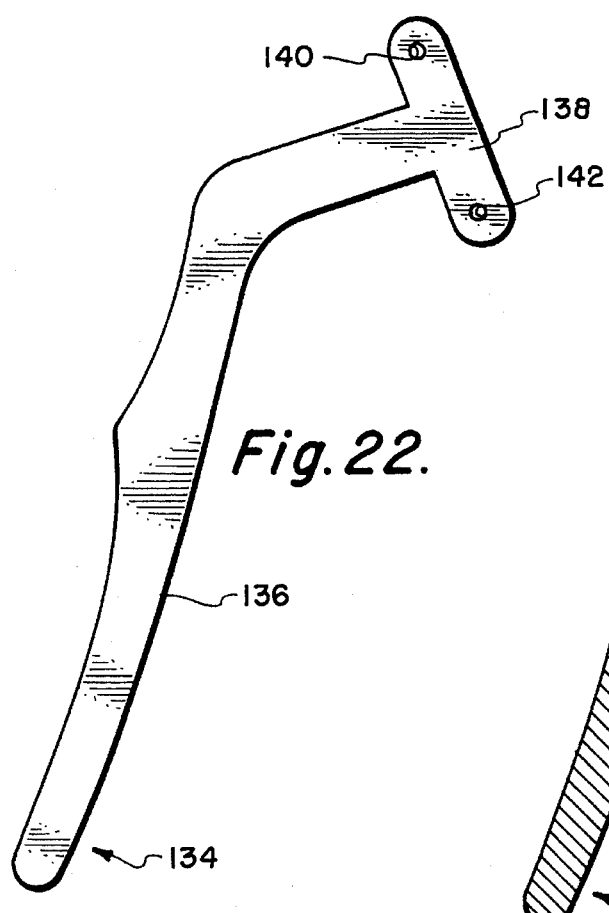
FIG. 22 is a side plan view of a trigger member, showing the location of two apertures in a support bar through which the trigger member will be installed for movement in the housing member illustrated in FIGS. 14 through 18.
Figure 23:
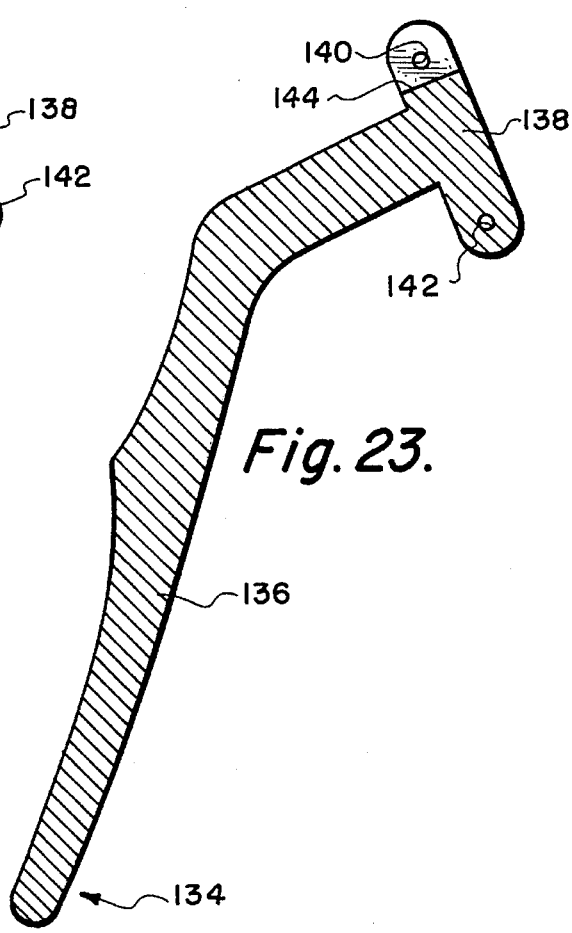
FIG. 23 is a cross-sectional view of the trigger member illustrated in FIG. 22, showing the slot located in one end of the support bar.
Figure 24:
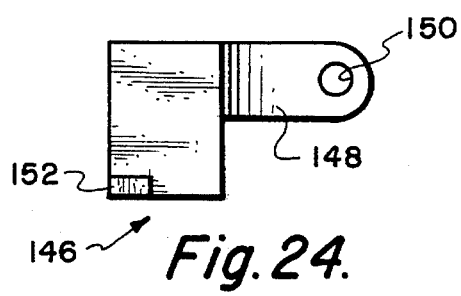
FIG. 24 is a side plan view of a slide member for mounting in the housing member illustrated in FIGS. 14 through 18, which slide member will engage and be actuated by the slotted end of the support bar of the trigger member illustrated in FIG. 23, and which slide member will also engage and operate the ball of the second shaft member illustrated in FIGS. 7 through 9.
Figure 26:
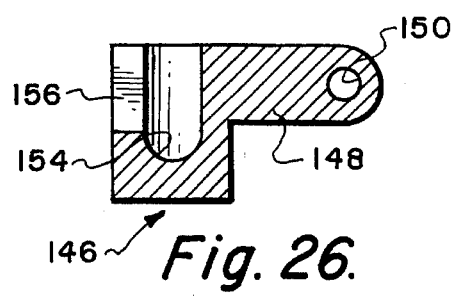
FIG. 26 is a cross-sectional view of the slide member illustrated in FIGS. 24 and 25, also showing the socket.
Figure 25:
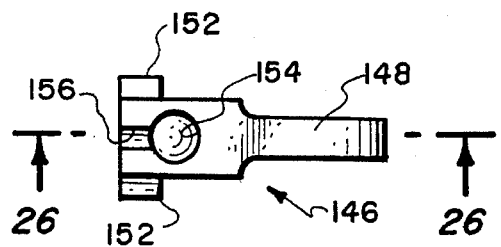
FIG. 25 is a top plan view of the slide member illustrated in FIG. 24, showing a socket for engaging the ball of the second shaft member illustrated in FIGS. 7 through 9, and also showing a slot communicating with the socket.
Figure 27:
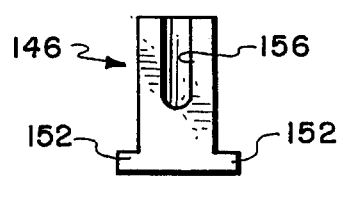
FIG. 27 is a front view the slide member illustrated in FIGS. 24 through 26, showing the slot communicating with the socket.

Referring next to FIGS. 22 and 23, a trigger member 134 is illustrated which includes a gripping portion 136 designed to be squeezed by the four fingers of a hand. Above the gripping portion 136, the trigger member 134 is angled back, and has a support bar 138 connected as the cross bar of a "T" at the end of the trigger member 134. The ends of the support bar 138 have apertures 140 and 142 laterally extending therethrough. The aperture 140 extends through the upper end of the support bar 138, while the aperture 142 extends through the lower end of the support bar 138.

The apertures 140 and 142 in the support bar 138 are the mechanism through which the trigger member 134 will be installed for movement in the housing member 84 (FIG. 16) using the slots 112 and 114. Located in the upper end of the support bar 138 is a notch 144 splitting the upper end of the support bar 138 into two lateral halves.

Referring now to FIGS. 24 through 27, a slide member 146 is illustrated. Extending from the rear of the slide member 146 near the top thereof is an arm 148 located in a vertical plane. The arm 148 has a lateral aperture 150 extending therethrough, and is for engagement with the notch 144 in the trigger member 134 (FIG. 23). Extending outwardly from the sides of the slide member 146 at the bottom and front thereof are horizontally oriented tabs 152, which are for engagement with the horizontal slots 106 in the left and right side walls 88 and 90 of the housing member 84 (FIGS. 16 and 18).

Located vertically in the top side of the slide member 146 is a cylindrical aperture forming a socket 154, which is for engaging the ball 66 of the second shaft member 64 (FIGS. 7 through 9). Located at the front of the socket 154 is a vertically extending slot 156 communicating with the socket 154. The slot 156 has a width designed to admit the shaft 68 through which the ball 66 is attached to the rest of the second shaft member 64 (FIG. 7).

Referring next to FIGS. 28 and 29, a locking member 158 used to selectively inhibit rotation of the wheel member 42 at the proximal end of the first shaft member (FIG. 6) is illustrated. The locking member 158 has a flat base member 160 which is of a width for placement in the notch 100 in the housing member 84 (FIGS. 15 and 17). Located on top of the flat base member 160 at the front thereof is a wedge member 162 designed to fit into the triangular notches 46 of the rectangular notch 44 of the wheel member 42 (FIG. 4) to inhibit rotation of the wheel member 42.

Extending upwardly from the rear of the flat base member 160 is an arm 164 which has a laterally extending aperture 166 therethrough. The aperture 166 will be used to pivotally mount the locking member 158 using the apertures 108 in the left and right side walls 88 and 90 of the housing member 84 (FIGS. 14, 16, and 18).

Referring next to FIG. 30, a pin 168 used to support the locking member 158 (FIGS. 28 and 29) is illustrated. The pin 168 has three sets of ridges located around the perimeter of the pin 168, each of which sets of ridges is used for frictional engagement of the pin 168 in an aperture. A center set of ridges 170 located in the middle of the pin 168 will be used to engage the aperture 166 in the arm 164 of the locking member 158. Sets of ridges 172 located at the ends of the pin 168 will be use to attach operating mechanisms to the ends of the locking member 158.

Referring next to FIG. 31, one of these operating mechanisms is illustrated. A lever 174 is illustrated which has an aperture 176 used for mounting the lever 174 onto one of the sets of ridges 172 on one end of the pin 168 (FIG. 30). The lever 174 may also have a raised portion 178 thereon to facilitate operation of the lever 174.

The assembly of the various components of FIGS. 14 through 31 may now be described. FIG. 32 illustrates the housing member 84 illustrated in FIGS. 14 through 18 with most of the left side wall 88 cut away for clarity. Assembled to the housing member 84 are the cover member 120 illustrated in FIGS. 19 through 21, the trigger member 134 illustrated in FIGS. 22 and 23, the slide member 146 illustrated in FIGS. 24 through 27, the locking member 158 illustrated in FIGS. 28 and 29, and the pin 168 illustrated in FIG. 30. Several additional components are illustrated as well.

The first component to be installed in the housing member 84 is the slide member 146. The slide member 146 is installed by placing it between the left and right side walls 88 and 90 of the housing member 84, with the tabs 152 of the slide member 146 fitting into the vertical slots 104 in the housing member 84. The slide member 146 is moved downwardly, so that the tabs 152 of the slide member 146 move to the bottoms of the vertical slots 104 in the housing member 84, which are in communication with the fronts of the horizontal slots 106 in the housing member 84. The slide member 146 is then moved toward the rear of the housing member 84, with the tabs 152 of the slide member 146 moving back in the horizontal slots 106 in the housing member 84.

The trigger member 134 may next be installed in the housing member 84, using two pins 180 and four bearings 182. One end of each of the pins 180 is peened, with the peened end being capable of retaining one of the bearings 182 thereon. The support bar 138 of the trigger member 134 is placed between the left and right side walls 88 and 90 of the housing member 84 with the aperture 140 in the support bar 138 aligned with the slots 112 in the housing member 84, and with the aperture 142 in the support bar 138 aligned with the slots 114 in the housing member 84.

One of the bearings 182 (not shown) is installed onto a first one of the pins 180, and the unpeened end of the first one of the pins 180 is inserted from the right side of the housing member 84 through the slot 112 (FIG. 16) in the right side wall 90 of the housing member 84. The arm 148 of the slide member 146 is then placed in the notch 144 (FIG. 23) in the support bar 138 of the trigger member 134, with the aperture 150 (FIG. 24) in the arm 148 aligned with the aperture 140 (FIGS. 22 and 23) of the support bar 138. The unpeened end of the first one of the pins 180 then goes through the aperture 140 in the support bar 138 of the trigger member 134 and the aperture 150 in the arm 148 of the slide member 146. The arm 148 of the slide member 146 is thereby retained and will be driven by movement of the top end of the support bar 138 of the trigger member 134.

The unpeened end of the first one of the pins 180 next goes through the slot 112 in the left side wall 88 (FIG. 14) of the housing member 84. Another one of the bearings 182 is then installed on the unpeened end of the first one of the pins 180. Both of the bearings 182 on the first one of the pins 180 fit fully into the slots 112 in the housing member 84, and the unpeened end of the first one of the pins 180 is then peened to retain it in place.

Another one of the bearings 182 (not shown) is installed onto a second one of the pins 180, and the unpeened end of the second one of the pins 180 is inserted from the right side of the housing member 84 through the slot 114 (FIG. 16) in the right side wall 90 of the housing member 84. The unpeened end of the second one of the pins 180 then goes through the aperture 142 (FIG. 22) in the support bar 138 of the trigger member 134, and through the slot 114 in the left side wall 88 (FIG. 14) of the housing member 84. The last one of the bearings 182 is then installed on the unpeened end of the second one of the pins 180. Both of the bearings 182 on the second one of the pins 180 fit fully into the slots 114 in the housing member 84, and the unpeened end of the second one of the pins 180 is then peened to retain it in place.

A spring member 184 having a roller wheel 186 located at one end thereof has the other end thereof secured to the front of the grip portion 86 of the housing member 84 with a screw 188 inserted into the threaded aperture 116 (FIG. 16). The spring member 184 biases the trigger member 134 into the position illustrated in FIG. 32. The gripping portion 136 of the trigger member 134 may be squeezed toward the grip portion 86 of the housing member 84, with the spring member 184 bearing on the back of the gripping portion 136 via the roller wheel 186 to resist such movement, and to return the trigger member 134 to the position shown when the squeezing pressure on the trigger member 134 is released.

It will also be appreciated by those skilled in the art that squeezing the gripping portion 136 of the trigger member 134 toward the grip portion 86 of the housing member 84 will cause the top end of the support bar 138 to drive the slide member 146 forward in the housing member 84. Upon releasing the squeezing pressure on the trigger member 134, the spring member 184 will return the trigger member 134 to the position illustrated, also driving the slide member 146 rearwardly to the position shown in FIG. 32.

A coil spring 190 is inserted into the cylindrical recess 102 in the housing member 84. The locking member 158 is inserted into the notch 100 with the wedge member 162 located at the front as shown. The aperture 166 (FIG. 28) in the arm 164 of the locking member 158 is aligned with the apertures 108 in the housing member 84, and the pin 168 is inserted through the aperture 108 in the right side of the housing member 84, through the aperture 166 in the arm 164 of the locking member 158, and then through the aperture 108 in the left side of the housing member 84.

The center set of ridges 170 (FIG. 30) of the pin 168 frictionally engage the aperture 166 in the arm 164 of the locking member 158, maintaining the arm 164 and the rest of the locking member 158 in a mounted position on the pin 168. The sets of ridges 172 (FIG. 30) on the ends of the pin 168 extend out of the apertures 108 on both sides of the housing member 84. Referring briefly to FIG. 34, one of the levers 174 will then be mounted on each of the sets of ridges 172 on the ends of the pin 168 (the mounting of a lever 174 on the right side of the housing member 84 is the same as illustrated on the left side in FIG. 34).

With the levers 174 being used on both sides of the housing member 84, operation of the locking member 158 may be done with the housing member 84 held in either hand of a user. Referring now to both FIGS. 32 and 34, by pushing end of the lever 174 having the raised portion 178 thereon upward, the wedge member 162 of the locking member 158 is moved downward against the force of the coil spring 190, and out of the cylindrical recess 94.

Referring again to FIG. 32, the installation of the cover member 120 may now be discussed. The cover member 120 is placed into position on the top of the housing member 84 as shown, with the slot 124 in the support arm 122 of the cover member 120 aligned with the apertures 110 (FIGS. 14 and 16) in the housing member 84. A pin 192 is installed in the apertures 110, extending through the slot 124 and thereby capturing the cover member 120. The pin 192 has an interference fit in the apertures 110, but not in the slot 124.

A spring member 194 has one end thereof secured to the front of the grip portion 86 of the housing member 84 with a screw 196 inserted into the threaded aperture 118 (FIG. 16). The other end of the spring member 194 extends back between the left and right side walls 88 and 90 of the housing member 84, and bears on the bottom of the support arm 122, urging it forward. Thus, it will be appreciated that the function of the spring member 194 is to urge the cover member 120 forward, to the limit of the slot 124 in the support arm 122 of the cover member 120.

It may be seen in FIG. 32 that the tabs 130 of the cover member 120 are captured by the notches 96 of the housing member 84 when the cover member 120 is in its forward position, into which it is urged by the spring member 194. Note again that the lengths of the tabs 130 on the cover member 120 are shorter than the lengths of the notches 96 in the housing member 84. This is to allow the cover member 120 to be pulled toward the rear of the housing member 84, as shown in FIG. 34. In this position, the tabs 130 of the cover member 120 are no longer captured by the notches 96 of the housing member 84, and the cover member 120 may be opened by rotating the front of the cover member 120 up and back, pivoting around the pin 192.

With the cover member 120 opened, the assembled first and second shaft members 40 and 64 may be installed in the manner illustrated in FIG. 34. The wheel member 42 of the first shaft member 40 fits into the cylindrical recess 94 (FIGS. 15 and 16) of the housing member 84, with the cylindrical segment 48 of the first shaft member 40 extending out of the housing member 84 through the cylindrical recess 92 (FIGS. 15 and 16) at the front of the housing member 84.

When the cover member 120 is closed as shown in FIG. 34, the wheel member 42 of the first shaft member 40 will be retained between the cylindrical recess 94 in the top of the housing member 84 and the cylindrical recess 128 (FIGS. 20 and 21) in the bottom of the cover member 120. Similarly, the cylindrical segment 48 of the first shaft member 40 will be retained between the cylindrical recess 92 in the top of the housing member 84 and the cylindrical recess 126 (FIGS. 20 and 21) in the bottom of the cover member 120. The tabs 130 of the cover member 120 are again retained by the notches 96 of the housing member 84.

It will be appreciated by those skilled in the art that the wedge member 162 of the locking member 158 (FIG. 32) will be urged by the coil spring 190 to engage one of the triangular notches 46 or the rectangular notch 44 (FIG. 5) in the wheel member 42 of the first shaft member 40 to retain the first shaft member 40 and the second shaft member 64 in a desired rotational configuration. This rotational configuration may be adjusted by pushing the raised portion 178 of one of the levers 174 upward to release the wedge member 162 of the locking member 158 from the engaged one of the triangular notches 46 or the rectangular notch 44 in the wheel member 42, then rotating the first shaft member 40 and the second shaft member 64 to their desired position and releasing the lever 174.

The operation of the rongeur surgical instrument of the present invention may now be discussed with reference to FIGS. 34 and 35. With the gripping portion 136 of the trigger member 134 in its unsqueezed position shown in FIG. 34, the distal end of the long top shaft 72 of the second shaft member 64 is in its fully proximal position on the flat surface 52 of the first shaft member 40. The cutting member 78 is thus far from the footplate 60. When the gripping portion 136 of the trigger member 134 is squeezed as shown in FIG. 35, the distal end of the long top shaft 72 of the second shaft member 64 moves to its fully distal position on the flat surface 52 of the first shaft member 40. The cutting member 78 is brought into contact with the footplate 60. During this operation any tissue or bone between the cutting member 78 and the footplate 60 will be cut.

In comparing the positions of the rongeur surgical instrument of the present invention shown in FIGS. 34 and 35, another difference is apparent. The pivot point is always at the location of the pin 180 and the bearings 182 in the slots 114. With the instrument in the position of FIG. 34, the pivot point is at the bottoms of the slots 114. In the position of the instrument in FIG. 35, the pivot point is at the tops of the slots 114.

It will thus be appreciated that during the actuation stroke, the pivot point will vary, becoming progressively shorter as the gripping portion 136 of the trigger member 134 is squeezed. Thus, as the cutting member 78 nears the footplate 60, a given movement of the gripping portion 136 of the trigger member 134 will produce progressively less and less movement of the cutting member 78, giving the operation a higher degree of precision of operation near the end of the stroke. This also moves the cutting member 78 faster during the first part of the stroke, when precision of operation is not needed as much.

This is graphically illustrated in the plot of FIG. 36, in which operation of a conventional rongeur is shown by the dotted line and the operation of the rongeur surgical instrument of the present invention is shown by the solid line. Throughout the stroke, the conventional rongeur retains a uniform mechanical advantage. However, the rongeur surgical instrument of the present invention has a smaller mechanical advantage at the beginning of the stroke, and the mechanical advantage increases throughout the stroke.

In addition to varying the speed and the precision of operation of the instrument, the amount of torque transmitted will also be varied throughout the stroke. At the beginning of the stroke, the torque will be at a minimum. This is fine, since little torque is needed, since the cutting operation does not take place at the beginning of the stroke. However, near the end of the stroke, the torque has increased; since this is the point at which the cutting operation will take place, this represents a highly desirable effect.

Figure 48:
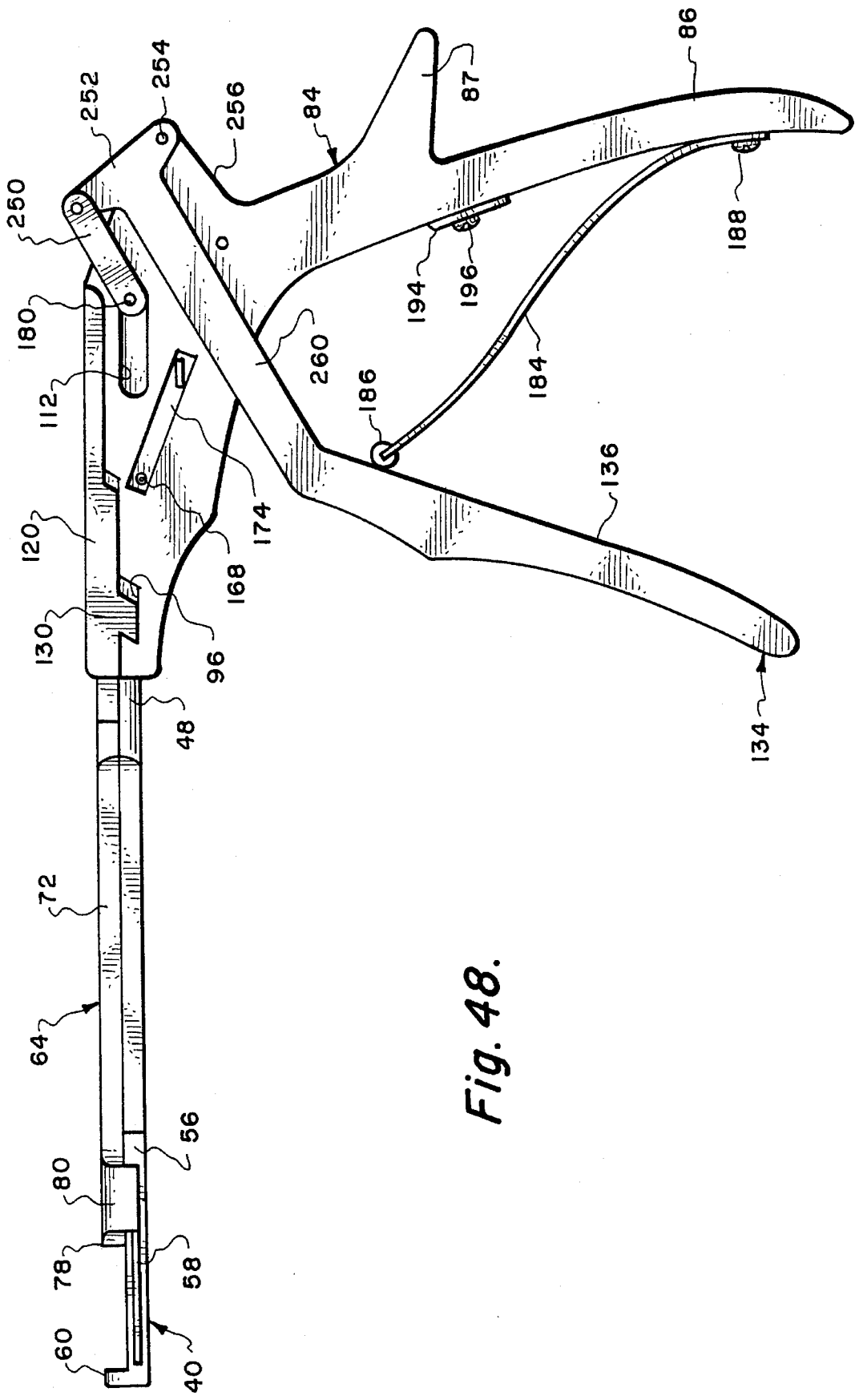
FIG. 48 is a plan view of an alternate embodiment of the invention similar to the plan view of the invention illustrated in FIG. 34. This alternate has one roller and one linkage in the actuating mechanism.

FIG. 48 illustrates an alternate embodiment of the actuating mechanism. The trigger member 134 is modified at its opposite end where the "T" end is located. The trigger member continues to have an elbow bend going to the "T" end 252. The "T" portion is longer and is forked beginning at the elbow bend. The forked portion 260 extends on both sides of the housing member 88 and fits around the housing member. The housing member 84 includes a rear projection 256 that is adjacent to the "T" end. The projection 256 has a hole and a pin 254 to secure the right half of the "T" 252 to the housing member. The stationary point for the actuating mechanism is located at the pin 254. The left end of the "T" has a linkage 250 connected to the roller and pin 180. There is another linkage 250 on the other side of the actuating mechanism that functions as a mirror image to linkage 250. Instead of being forked at the "T" portion, the "T" portion can be flat and able to fit in the housing 84. In this version, the right side of the "T" would be fastened to the stationary point 254 by being placed between the walls of the housing member at the projection 252.

Figure 49:
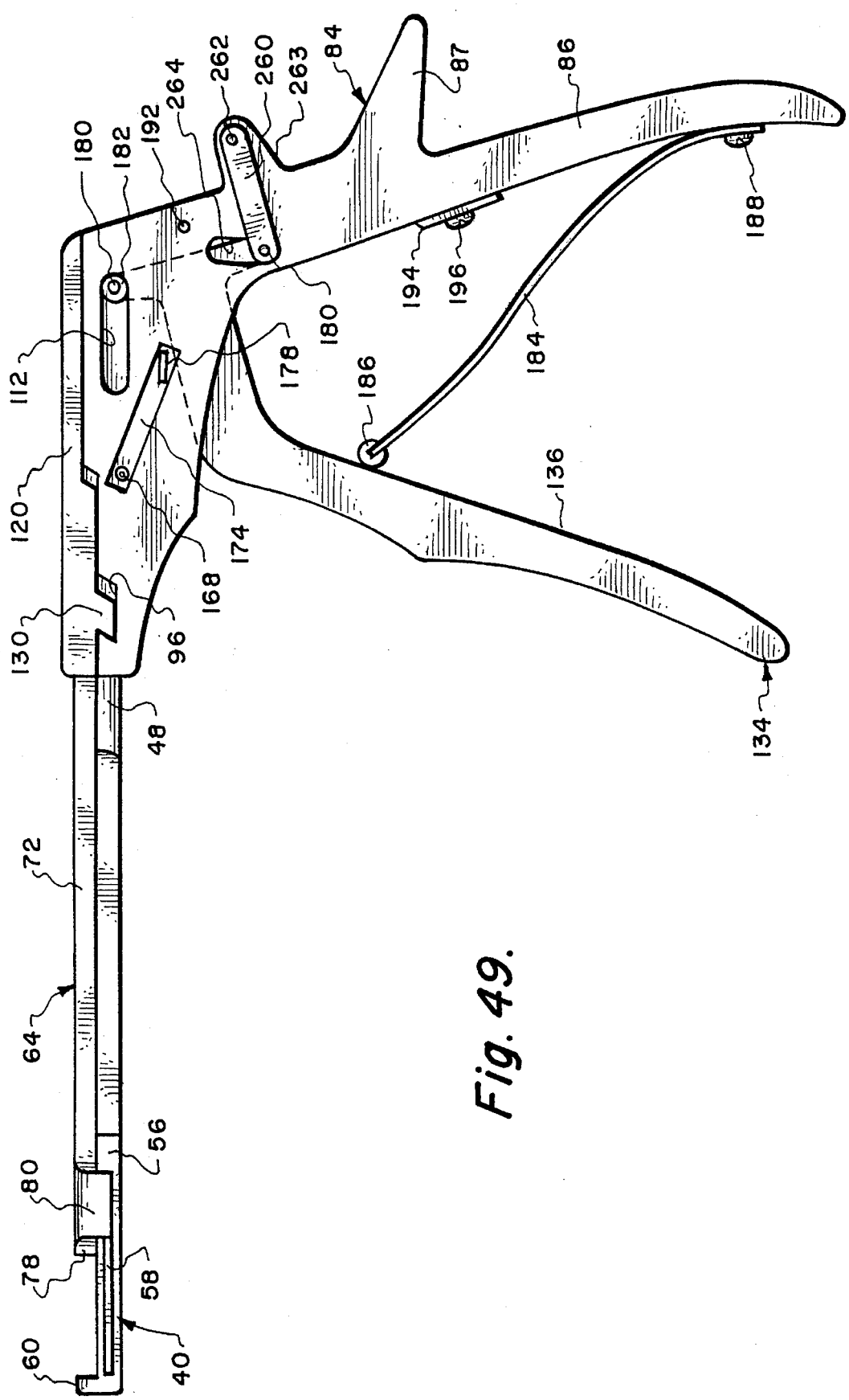
FIG. 49 is a plan view of another alternate embodiment of the invention similar to the plan view of the invention illustrated in FIG. 34. This alternate embodiment has the actuating mechanism changed. It has one roller and one linkage arranged in a different configuration than the alternate embodiment in FIG. 48.

FIG. 49 illustrates another alternate embodiment of the actuating mechanism. The trigger member 134 is the same configuration as shown in the preferred embodiment in FIG. 34. However, the stationary point for the actuating mechanism is now at 262. There is a projection 263 above the spur 87. The right half of the "T" moves along the slot 264 rather than remaining stationary and pivoting as is the case in the alternate shown in FIG. 48. An additional pair of linkages 260 are on both sides of the housing member 84. The other ends of the pair of linkages 260 are secured to the roller by a pin 180. The slotted opening 264 is changed slightly to allow the roller and pin 180 clearance to move as the actuating mechanism is being used.

In an alternate embodiment, the housing member 84 of FIGS. 14 through 18 may be modified to replace the spur member 87, which is mounted in a fixed position on the rear of the grip portion 86 (FIGS. 14 and 16), with an adjustable spur member mounted on the grip portion 86 in a position which may be adjusted. This adjustment will vary the height of the spur member on the rear of the grip portion 86.

Referring to FIGS. 37 through 39, a housing member 198 having a grip portion 200 is illustrated which is identical to the housing member 84 of FIGS. 14 through 18, with three exceptions. First, unlike the grip portion 86, the grip portion 200 of the housing member 198 does not have a fixed spur member 87 mounted thereon. Second, the rear of the grip portion 200 has a flat portion 202 near the location corresponding to the location of the spur member 87 on the grip portion 86. Third, the sides of the grip portion 200 have slots 204 and 206 in the left and right sides, respectively, thereof in front of the flat portion 202.

The flat portion 202 on the rear of the grip portion 200 of the housing member 198 extends upward and downward somewhat from the location of the spur member 87 on the grip portion 86. The slots 204 and 206 are spaced away from and parallel to the flat portion 202, and also upward and downward somewhat from the location of the spur member 87 on the grip portion 86. In all other respects, the housing member 198 is the same as the housing member 84, and reference numerals identical to those used on the housing member 84 are used on similar components on the housing member 198.

Referring next to FIGS. 40 through 42, a left adjustable spur half 208 is illustrated which has a main portion similar in configuration to the left half of the spur member 87 (FIGS. 14 and 16). The left adjustable spur half 208 has an arm 210 extending from the lower left front portion thereof, which arm 210 is configured to fit around the left side of the portion of the grip portion 200 having the slot 204 therein (FIGS. 37 through 39). On the right-facing side of the arm 210 is a tab 212 which is oriented to fit into the slot 204. Note that the length of the tab 212 is considerably less then the length of the slot 204.

Extending through the main portion of the left adjustable spur half 208 is an aperture 214, which is countersunk on the left side of the left adjustable spur half 208. Also located in the main portion of the left adjustable spur half 208 on the right side thereof and spaced away from the aperture 214 is an aperture 216 which does not extend through the left adjustable spur half 208.

Referring next to FIGS. 43 through 45, a right adjustable spur half 218 is illustrated which has a main portion similar in configuration to the right half of the spur member 87 (FIGS. 14 and 16). The right adjustable spur half 218 has an arm 220 extending from the lower right front portion thereof, which arm 220 is configured to fit around the right side of the portion of the grip portion 200 having the slot 206 therein (FIGS. 37 through 39). On the left-facing side of the arm 220 is a tab 222 which is oriented to fit into the slot 206. Note that the length of the tab 222 is considerably less then the length of the slot 206.

Extending into the left side of the main portion of the right adjustable spur half 218 is a threaded aperture 224, which does not extend through the right adjustable spur half 218. The location of the threaded aperture 224 in the right adjustable spur half 218 corresponds exactly to the location of the aperture 214 in the left adjustable spur half 208 (FIG. 41). Extending from the left side of the main portion of the right adjustable spur half 218 and spaced away from the aperture 224 is a pin 226, the location of which pin 226 in the right adjustable spur half 218 corresponds exactly to the location of the aperture 216 in the left adjustable spur half 208 (FIG. 41). In addition, the pin 226 is sized to fit into the aperture 216.

Figure 46:
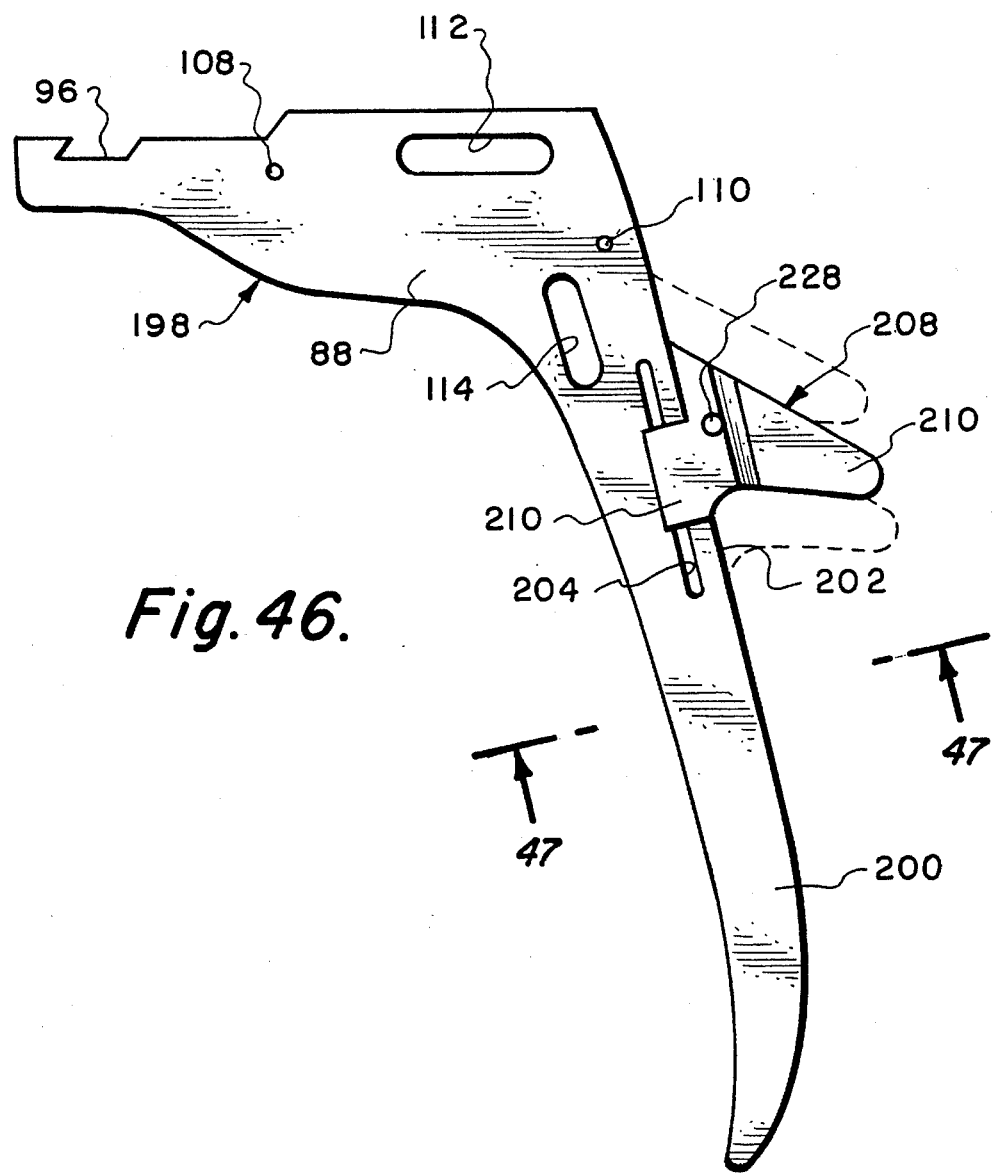
FIG. 46 is a side plan view of the alternate embodiment housing member illustrated in FIGS. 37 through 39, showing an adjustable spur assembly consisting of the left adjustable spur half illustrated in FIGS. 40 through 42 and the right adjustable spur half illustrated in FIGS. 43 through 45 mounted on the rear of the grip portion of the alternate embodiment housing member.
Figure 47:
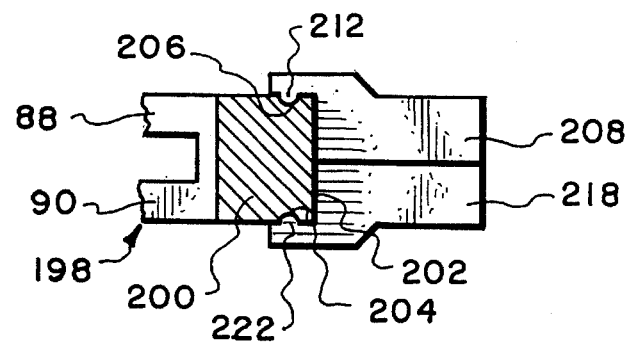
FIG. 47 is a cross-sectional view of the alternate embodiment housing member and the adjustable spur assembly illustrated in FIG. 46, showing the fit of the tabs of the left and right adjustable spur halves in the slots in the left and right sides of the grip portion of the alternate embodiment housing member.

Referring now to FIGS. 46 and 47, the assembly of the left adjustable spur half 208 and the right adjustable spur half 218 to the grip portion 200 of the housing member 198 is illustrated. The left adjustable spur half 208 is positioned with the tab 212 of the left adjustable spur half 208 in the slot 204 of the grip portion 200, and the right adjustable spur half 218 is positioned with the tab 222 of the right adjustable spur half 218 in the slot 206 of the grip portion 200. The right side of the main portion of the left adjustable spur half 208 is brought into contact with the left side of the main portion of the right adjustable spur half 218, with the pin 226 of the right adjustable spur half 218 extending into the aperture 216 of the left adjustable spur half 208.

A flat head screw 228 is installed through the aperture 214 in the left adjustable spur half 208 into the threaded aperture 224 in the right adjustable spur half 218. By not quite tightening the flat head screw 228, the adjustable spur assembly consisting of the left adjustable spur half 208 and the right adjustable spur half 218 may be adjusted in height on the grip portion 200 of the housing member 198. When the adjustable spur assembly is properly positioned, the flat head screw 228 may be tightened to fix the adjustable spur assembly in place on the grip portion 200 of the housing member 198.

It may therefore be appreciated from the above detailed description of the preferred embodiment of the present invention that it teaches a more positive mechanism for maintaining the relative alignment of the cutting member and the footplate in a rongeur surgical instrument. The mechanism for maintaining alignment of the cutting member and the footplate does not interfere in any way with the cutting operation of the surgical instrument, or with the surgeon's vision of the cutting operation. In addition, this desirable design ambition is achieved without increasing the size of the members in any way, thereby maintaining a small distal shaft configuration.

In another primary aspect, the present invention provides a variable degree of mechanical advantage to the trigger-actuated operation of the movement of the cutting member toward the footplate. During initial actuation of the trigger member to initiate movement of the cutting member toward the footplate prior to engagement of bone or tissue, the improved rongeur surgical instrument provides a lesser degree of mechanical advantage, together with a greater degree of movement of the cutting member. In contrast, during actuation of the trigger subsequent to engagement of bone or tissue between the cutting member and the footplate, the improved rongeur surgical instrument provides a greater degree of mechanical advantage, together with a lesser degree of movement of the cutting member.

In still another primary aspect, the present invention provides a mechanism for inhibiting movement of bone or tissue chips, once cut, distally out of the tunnel in the cutting member. This mechanism thus provides a restriction on the movement of the bone or tissue chips, but without restricting in any way the cutting operation of the surgical instrument. Thus, the mechanism for inhibiting movement of bone or tissue chips to the location of the cutting operation should enhance the ease of the cutting operation by not requiring the surgeon to pause to remove bone or tissue chips from the cutting members.

The rongeur surgical instrument of the present invention also provides a grip which is adjustable to provide a custom fit to a wide variety of hand sizes. The variable fit of the grip may be modified to provide a comfortable accommodation for any hand size through a simple adjustment which may be quickly and easily accomplished. It can be appreciated that the invention disclosed and claimed herein can be used and incorporated herein with various tools and instruments other than a rongeur, such as staplers, tonsil and adenoid cutters, etc. The improved rongeur surgical instrument of the present invention is of solid construction, to be both durable and long-lasting in operation. Finally, all of the aforesaid advantages and objectives of the present invention are achieved without incurring any substantial relative disadvantage.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A surgical instrument comprising:

an elongated first shaft member having a distal end and a proximal end;

a footplate mounted at the distal end of said first shaft member and extending generally transversely to said first shaft member;

an elongated second shaft member having a distal end and a proximal end, said second shaft member being mounted adjacent said first shaft member for reciprocating movement relative thereto;

cutting means located at said distal end of said second shaft member, said second shaft member being moveable between a first position in which said cutting means is spaced away from said footplate and a second position in which said cutting means is abutting said footplate;

said cutting means comprises a U-shaped segment having a sharpened cutting edge at said distal end of said second shaft member;

an aperture in said U-shaped segment disposed in the base of the U in said U-shaped segment and at the end of said U-shaped segment closest to said proximal end of said second shaft member;

means for actuating said surgical instrument, said actuating means being moveable between a first position and a second position; and means for operatively connecting said actuating means to drive said second shaft member, said connecting means operating to vary the nature of the linkage between said actuating means and said second shaft member.

2. A surgical instrument comprising:

an elongated first shaft member having a distal end and a proximal end;

a footplate mounted at the distal end of said first shaft member and extending generally transversely to said first shaft member;

an elongated second shaft member having a distal end and a proximal end, said second shaft member being mounted adjacent said first shaft member for reciprocating movement relative thereto;

cutting means located at said distal end of said second shaft member, said second shaft member being moveable between a first position in which said cutting means is spaced away from said footplate and a second position in which said cutting means is abutting said footplate;

said cutting means comprises a U-shaped segment having a sharpened cutting edge at said distal end of said second shaft member;

means for actuating said surgical instrument, said actuating means being moveable between a first position and a second position;

means for operatively connecting said actuating means to drive said second shaft member, said connecting means operating to vary the nature of the linkage between said actuating means and said second shaft member; and means for facilitating movement of any bone or tissue chips which may be inside said U-shaped member in a direction toward the proximal end of said first shaft member, and for impeding movement of any bone or tissue chips which may be inside said U-shaped member in a direction toward the distal end of said first shaft member.

3. A surgical instrument comprising:

an elongated first shaft member having a distal end and a proximal end;

a footplate mounted at the distal end of said first shaft member and extending generally transversely to said first shaft member;

an elongated second shaft member having a distal end and a proximal end, said second shaft member being mounted adjacent said first shaft member for reciprocating movement relative thereto;

U-shaped segment having a sharpened cutting edge located at said distal end of said second shaft member, the open side of said U-shaped segment faces a side of said first shaft member;

said second shaft member being moveable between a first position in which said cutting means is spaced away from said footplate and a second position in which said cutting means is abutting said footplate;

means for facilitating movement of any bone or tissue chips which may be inside said U-shaped segment in a direction toward the proximal end of said first shaft member, and for impeding movement of any bone or tissue chips which may be inside said U-shaped segment in a direction toward the distal end of said first shaft member;

said means for facilitating and impeding movement of any bone or tissue chips comprises:
  a plurality of grooves located in the side of said first shaft member faced by said open side of said U-shaped segment, said plurality of grooves being configured to facilitate movement of any bone or tissue chips which may be inside said U-shaped segment in a direction toward the proximal end of said first shaft member, and to impede movement of any bone or tissue chips which may be inside said U-shaped segment in a direction toward the distal end of said first shaft member;

means for actuating said surgical instrument, said actuating means being moveable between a first position and a second position; and means for operatively connecting said actuating means to drive said second shaft member, said connecting means operating to vary the nature of the linkage between said actuating means and said second shaft member.

4. A surgical instrument as defined in claim 3, wherein the edge of each of said grooves closest to said proximal end of said first shaft member are tapered, and the edge of each of said grooves closest to said distal end of said first shaft member are essentially orthogonal to the side of said first shaft member faced by said open side of said U-shaped member.

5. A surgical instrument comprising:
  an elongated first shaft member having a distal end and a proximal end;
  a footplate mounted at the distal end of said first shaft member and extending generally transversely to said first shaft member;
  an elongated second shaft member having a distal end and a proximal end, said second shaft member being mounted adjacent said first shaft member for reciprocating movement relative thereto;
  cutting means located at said distal end of said second shaft member, said second shaft member being moveable between a first position in which said cutting means is spaced away from said footplate and a second position in which said cutting means is abutting said footplate;
  means for retaining said distal end of said second shaft member in close proximity to said distal end of said first shaft member;
  said retaining means comprises:
    longitudinal slots in the sides of said first shaft member;
    side members extending from the sides of said second shaft member around the sides of said first shaft member over said slots in said first shaft member; and
    inwardly extending tabs mounted on the sides of said side members facing said first shaft member, said tabs for engagement within said slots in said first shaft member;
  means for actuating said surgical instrument, said actuating means being moveable between a first position and a second position; and
  means for operatively connecting said actuating means to drive said second shaft member, said connecting means operating to vary the nature of the linkage between said actuating means and said second shaft member.

6. A surgical instrument as defined in claim 5, wherein said slots and tabs are arranged and configured to prevent said tabs from moving radially outwardly out of said slots.

7. A surgical instrument as defined in claim 6, wherein said slots widen in cross-section as they extend into the sides of said first shaft member, and wherein said tabs widen in cross-section as they extend inwardly.

8. A surgical instrument as defined in claim 7, additionally comprising:
  a narrowed width segment disposed on said first shaft member proximally of said slots, said narrowed width segment being in mechanical communication with said slots to allow said tabs to initially fit over said first shaft member to be installed into said slots.

9. A surgical instrument comprising:
  an elongated first shaft member having a distal end and a proximal end;
  a footplate mounted at the distal end of said first shaft member and extending generally transversely to said first shaft member;
  an elongated second shaft member having a distal end and a proximal end, said second shaft member being mounted adjacent said first shaft member for reciprocating movement relative thereto;
  cutting means located at said distal end of said second shaft member, said second shaft member being moveable between a first position in which said cutting means is spaced away from said footplate and a second position in which said cutting means is abutting said footplate;
  means for actuating said surgical instrument, said actuating means being moveable between a first position and a second position;
  means for operatively connecting said actuating means to drive said second shaft member, said connecting means operating to vary the nature of the linkage between said actuating means and said second shaft member;
  a housing member having an open top side, said housing member having means for receiving said proximal end of said first shaft member in said open top side thereof; and
  a cover member for installation over said open top side of said housing member to retain said proximal end of said first shaft member in said housing member.

10. A surgical instrument as defined in claim 9, wherein said first shaft member has a wheel member mounted at said proximal end thereof, said wheel member being received in said housing member, said surgical instrument additionally comprising:
  means for limiting rotational movement of said first shaft member.

11. A surgical instrument as defined in claim 10, wherein said limiting means comprises:
  a plurality of notches located in the outer periphery of said wheel member;
  means, mounted in said housing member, for bearing against said wheel member in one of said notches to prevent rotational movement of said wheel member; and
  means for manually moving said means for bearing against said wheel member to prevent rotational movement of said wheel member away from said wheel member to allow said wheel member to be rotated.

12. A surgical instrument as defined in claim 11, wherein said moving means may be operated from either side of said housing member.

13. A surgical instrument as defined in claim 9, additionally comprising:

means for gripping said housing member, said gripping means being mounted on said housing member in a pistol-like manner;

and wherein said actuating means comprises:

a trigger member.

14. A surgical instrument as defined in claim 13, wherein said gripping means comprises:

a grip portion extending downwardly from the rear of said housing member, said grip portion being adapted for placement in the palm of a human hand; and means for adjusting the fit of said grip portion to accommodate various sizes of human hands.

15. A surgical instrument as defined in claim 14, wherein said adjusting means comprises:

an adjustable spur member extending from the rear of said grip portion, said adjustable spur member being moveable in position relatively higher or lower on said grip portion.

16. A surgical instrument as defined in claim 15, wherein said adjustable spur member comprises:

a left adjustable spur half; and a right adjustable spur half.

17. A surgical instrument as defined in claim 16, wherein said grip portion has a left side, a right side, and a rear surface, and comprises:

a slot located in each of said left and right sides of said grip portion parallel to said rear surface of said grip portion;

and wherein said left adjustable spur half comprises:

a left arm overlaying a portion of said left side of said grip portion including a portion of said slot located in said left side of said grip portion; and a first tab extending from the right side of said left arm into a portion of said slot located in said left side of said grip portion;

and wherein said right adjustable spur half comprises:

a right arm overlaying a portion of said right side of said grip portion including a portion of said slot located in said right side of said grip portion; and a second tab extending from the left side of said right arm into a portion of said slot located in said right side of said grip portion.

18. A surgical instrument as defined in claim 16, wherein said adjusting means further comprises:

screw means for attaching said left adjustable spur half to said right adjustable spur half, said adjustable spur member being moveable in position relatively higher or lower on said grip portion when said screw means is loosened, and said adjustable spur member being fixed in position on said grip portion when said screw means is tightened.

19. A surgical instrument as defined in claim 9, additionally comprising:

spring means for biasing said actuating means toward said first position.

20. A surgical instrument as defined in claim 9, wherein said connecting means comprises:

a drive member mounted in said housing for reciprocating movement toward the front and rear of said housing member, said second shaft member being connected to be driven by reciprocating movement of said drive member; and means coupled between said actuating means and said drive member for varying the degree of movement of said second shaft member caused by a given movement of said actuating means.

21. A surgical instrument as defined in claim 20, wherein said means coupled between said actuating means and said drive member varies the degree of movement of said second shaft member caused by a given movement of said actuating means by varying the pivot point about which said actuating means operates.

22. A surgical instrument as defined in claim 21, wherein said means coupled between said actuating means and said drive member comprises:

a support member having a first end and a second end, said first end of said support member being connected to drive said drive member, an intermediate portion of said support member being connected to said actuating means, and said second end of said support member moving up and down in a defined path relative to said housing member.

23. A surgical instrument as defined in claim 20, wherein said drive member has a socket therein, and wherein said proximal end of said second shaft member has a ball member thereon, said ball member being received in said socket.

24. A surgical instrument comprising:

an elongated first shaft member having a distal end and a proximal end;

a footplate mounted at the distal end of said first shaft member and extending generally transversely to said first shaft member;

an elongated second shaft member having a distal end and a proximal end, said second shaft member being mounted adjacent said first shaft member for reciprocating movement relative thereto;

cutting means located at said distal end of said second shaft member, said second shaft member being moveable between a first position in which said cutting means is spaced away from said footplate and a second position in which said cutting means is abutting said footplate;

a housing member having an open top side, said housing member having means for receiving said proximal end of said first shaft member in said open top side thereof;

a cover member for installation over said open top side of said housing member to retain said proximal end of said first shaft member in said housing member;

said cover member is hingedly connected at the rear thereof to said housing member;

means for latching said cover member in a closed position on said housing member;

means for actuating said surgical instrument, said actuating means being moveable between a first position and a second position; and means for operatively connecting said actuating means to drive said second shaft member, said connecting means operating to vary the nature of the linkage between said actuating means and said second shaft member.

25. A surgical instrument as defined in claim 24, wherein said latching means comprises:

a plurality of tabs extending from the bottom of said cover member at the sides and near the front thereof;

a plurality of notches in the top of said housing member at the sides and near the front thereof, said tabs for engagement with said notches to retain said cover member in a closed position, said cover member having a limited degree of movement toward the rear of said housing member to release said tabs from said notches; and means for urging said cover member toward the front of said housing member.

26. A surgical instrument, comprising:

an elongated first shaft member having a distal end and a proximal end;

a footplate mounted at the distal end of said first shaft member and extending generally transversely to said first shaft member;

an elongated second shaft member having a distal end and a proximal end, said second shaft member being mounted adjacent said first shaft member for reciprocating movement relative thereto;

a U-shaped segment having a sharpened cutting edge located at said distal end of said second shaft member, said second shaft member being moveable between a first position in which said sharpened cutting edge is spaced away from said footplate and a second position in which said sharpened cutting edge is abutting said footplate;

trigger means for driving said second shaft member from said first position to said second position; and means for facilitating movement of any bone or tissue chips which may be inside said U-shaped member in a direction toward the proximal end of said first shaft member, and for impeding movement of any bone or tissue chips which may be inside said U-shaped member in a direction toward the distal end of said first shaft member.

27. A surgical instrument comprising:

an elongated first shaft member having a distal end and a proximal end;

a footplate mounted at the distal end of said first shaft member and extending generally transversely to said first shaft member;

an elongated second shaft member having a distal end and a proximal end, said second shaft member being mounted adjacent said first shaft member for reciprocating movement relative thereto;

U-shaped segment having a sharpened cutting edge located at said distal end of said second shaft member, the open side of said U-shaped segment faces a side of said first shaft member;

said second shaft member being moveable between a first position in which said cutting means is spaced away from said footplate and a second position in which said cutting means is abutting said footplate;

trigger means for driving said second shaft member from said first position to said second position;

means for facilitating movement of any bone or tissue chips which may be inside said U-shaped member in a direction toward the proximal end of said first shaft member, and for impeding movement of any bone or tissue chips which may be inside said U-shaped member in a direction toward the distal end of said first shaft member;

said means for facilitating and impeding any movement of bone or tissue chips comprises:

a plurality of grooves located in the side of said first shaft member faced by said open side of said U-shaped member, said plurality of grooves being configured to facilitate movement of any bone or tissue chips which may be inside said U-shaped member in a direction toward the proximal end of said first shaft member, and to impede movement of any bone or tissue chips which may be inside said U-shaped member in a direction toward the distal end of said first shaft member.

28. A surgical instrument as defined in claim 27, wherein the edge of each of said grooves closest to said proximal end of said first shaft member are tapered, and the edge of each of said grooves closest to said distal end of said first shaft member are essentially orthogonal to the side of said first shaft member faced by said open side of said U-shaped member.

29. A surgical instrument comprising:

an elongated first shaft member having a distal end and a proximal end;

longitudinal slots in the sides of said first shaft member;

a footplate mounted at the distal end of said first shaft member and extending generally transversely to said first shaft member;

an elongated second shaft member having a distal end and a proximal end, said second shaft member being mounted adjacent said first shaft member for reciprocating movement relative thereto;

cutting means located at said distal end of said second shaft member, said second shaft member being moveable between a first position in which said cutting means is spaced away from said footplate and a second position in which said cutting means is abutting said footplate;

side members extending from the sides of said second shaft member around the sides of said first shaft member over said slots in said first shaft member;

inwardly extending tabs mounted on the sides of said side members facing said first shaft member, said tabs for engagement within said slots in said first shaft member;

means for retaining said distal end of said second shaft member in close proximity to said distal end of said first shaft member; and trigger means for driving said second shaft member from said first position to said second position.

30. A surgical instrument as defined in claim 29, wherein said slots and tabs are arranged and configured to prevent said tabs from moving radially outwardly out of said slots.

31. A surgical instrument as defined in claim 30, wherein said slots widen in cross-section as they extend into the sides of said first shaft member, and wherein said tabs widen in cross-section as they extend inwardly.

32. A surgical instrument as defined in claim 31, additionally comprising:

a narrowed width segment disposed on said first shaft member proximally of said slots, said narrowed width segment being in mechanical communication with said slots to allow said tabs to initially fit over said first shaft member to be installed into said slots.

33. A surgical instrument, comprising:

a housing member having a front portion and a rear portion;

a grip portion extending downwardly from the rear portion of said housing member, said grip portion being adapted for placement in the palm of a human hand;

means for adjusting the fit of said grip portion to accommodate various sizes of human hands;

said means for adjusting the fit of said grip portion to accommodate various sizes of human hands comprises:

an adjustable spur member extending from the rear of said grip portion, said adjustable spur member being movable in position relatively higher or lower on said grip portion;

an elongated first shaft member having a distal end and a proximal end, the proximal end of said first shaft member being mounted in said front portion of said housing member;

a footplate mounted at the distal end of said first shaft member and extending generally transversely to said first shaft member;

an elongated second shaft member having a distal end and a proximal end, said second shaft member being mounted adjacent said first shaft member for reciprocating movement relative thereto;

cutting means located at said distal end of said second shaft member, said second shaft member being moveable between a first position in which said cutting means is spaced away from said footplate and a second position in which said cutting means is abutting said footplate; and trigger means mounted in said housing member for driving said second shaft member from said first position to said second position.

34. A surgical instrument as defined in claim 33, wherein said adjustable spur member comprises:

a left adjustable spur half; and a right adjustable spur half.

35. A surgical instrument as defined in claim 34, wherein said grip portion has a left side, a right side, and a rear surface, and comprises:

a slot located in each of said left and right sides of said grip portion parallel to said rear surface of said grip portion;

and wherein said left adjustable spur half comprises:

a left arm overlaying a portion of said left side of said grip portion including a portion of said slot located in said left side of said grip portion; and a first tab extending from the right side of said left arm into a portion of said slot located in said left side of said grip portion;

and wherein said right adjustable spur half comprises:

a right arm overlaying a portion of said right side of said grip portion including a portion of said slot located in said right side of said grip portion; and a second tab extending from the left side of said right arm into a portion of said slot located in said right side of said grip portion.

36. A surgical instrument as defined in claim 34, wherein said adjusting means further comprises:

screw means for attaching said left adjustable spur half to said right adjustable spur half, said adjustable spur member being moveable in position relatively higher or lower on said grip portion when said screw means is loosened, and said adjustable spur member being fixed in position on said grip portion when said screw means is tightened.

* * * * *